US009631236B2

(12) United States Patent
Goren et al.

(10) Patent No.: US 9,631,236 B2
(45) Date of Patent: Apr. 25, 2017

(54) METHODS AND COMPOSITIONS FOR DETERMINING HEART FAILURE OR A RISK OF HEART FAILURE

(75) Inventors: Yaron Goren, Kefar Hess (IL); Ofer Amir, Haifa (IL)

(73) Assignees: Rosetta Genomics Ltd., Rehovot (IL); MOR Research Applications Ltd., Tel Aviv (IL)

( * ) Notice: Subject to any disclaimer, the term of this patent is extended or adjusted under 35 U.S.C. 154(b) by 453 days.

(21) Appl. No.: 14/119,425

(22) PCT Filed: May 23, 2012

(86) PCT No.: PCT/IL2012/000201

§ 371 (c)(1),
(2), (4) Date: Mar. 6, 2014

(87) PCT Pub. No.: WO2012/160551

PCT Pub. Date: Nov. 29, 2012

(65) Prior Publication Data

US 2014/0171400 A1 Jun. 19, 2014

Related U.S. Application Data

(60) Provisional application No. 61/489,272, filed on May 24, 2011.

(51) Int. Cl.
*C12Q 1/68* (2006.01)
*C12P 19/34* (2006.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 5,541,308 A * 7/1996 Hogan ................. C12Q 1/6811 435/6.12
2010/0047784 A1 2/2010 Shlomit et al.
2011/0086348 A1 4/2011 Prasad et al.
2011/0144914 A1* 6/2011 Harrington .......... C12Q 1/6883 702/19

FOREIGN PATENT DOCUMENTS

WO WO 2009/147656 A1 12/2009
WO WO 2010/058393 A2 5/2010
WO WO 2010/126370 A2 11/2010

OTHER PUBLICATIONS

Cobb et al (Crit Care Med 2002 vol. 30 p. 2711).*
Cheung et al (Cold Spring Harbory Symposia on Quant Biol, 2003, vol. LXVIII, pp. 403-407).*
Hoshikawa et al (Physiol. Genomics, 2003, 12: 209-219).*
Enard et al. (Science 2002 vol. 296 p. 340).*
Buck et al (Biotechniques (1999) 27(3):528-536).*
XP002731933 "Human-derived RT-PCR reverse primer, SEQ:100" retrieved from EBI accession No. GSN:AYC13971 Database accession No. AYC13971 *sequence * Jul. 22, 2010.
XP002731934 "Human short hairpin RNA hsa-miR-423-3p, SEQ:42." retrieved from EBI accession No. GSN:AYC13913 Database accession No. AYC13913 *sequence *Jul. 22, 2010.
XP002731935 "Gastric cancer related hairpin miRNA, hsa-miR-423-5p, SEQ ID 46.", retrieved from EBI accession No. GSN:AXV95911, Database accession No. AXV95911,*sequence * Apr. 15, 2010.
EP Search Report dated Nov. 21, 2014.
XP002731936 "Gastric cancer related miRNA, hsa-miR-423-5p, SEQ ID 39.", retrieved from EBI accession No. GSN:AXV95904, Database accession No. AXV95904,*sequence * Apr. 15, 2010.
Huang et al. "MicroRNAs in Cardiac Remodeling and Diseases," Journal of Cardiovascular Translational Research, Feb. 17, 2010, vol. 3, pp. 212-218.
Markham et al. "MicroRNAs and Heart Failure Diagnosis MiR-acle or MiR-age?," Circulation Research, Apr. 2, 2010, vol. 106, pp. 1011-1013.
Goren et al. "Serum Levels of MicroRNa's in Patients with Heart Failure," European Journal of Heart Failure, Nov. 25, 2011, vol. 14, pp. 147-154.
PCT Search Report WO 2012/160551 A1 dated Dec. 7, 2012.

* cited by examiner

*Primary Examiner* — Sarae Bausch
(74) *Attorney, Agent, or Firm* — Polsinelli PC; Ron Galant

(57) ABSTRACT

The present invention is based in part on the discovery of a panel of miRs whose levels are increased or decreased in the circulation of chronic systolic HF patients. Accordingly, an extensive panel of miRs was screened in the sera of stable chronic systolic HF patients and the results were compared to an age, gender and ethnically matched control group.

12 Claims, 9 Drawing Sheets

SEQUENCE LISTING

```
<160> NUMBER OF SEQ ID NOS: 196

<210> SEQ ID NO 1
<211> LENGTH: 22
<212> TYPE: RNA
<213> ORGANISM: Homo sapiens

<400> SEQUENCE: 1

aaaagcuggg uugagagggc ga                                              22


<210> SEQ ID NO 2
<211> LENGTH: 22
<212> TYPE: RNA
<213> ORGANISM: Homo sapiens

<400> SEQUENCE: 2

acugcaguga aggcacuugu ag                                              22


<210> SEQ ID NO 3
<211> LENGTH: 22
<212> TYPE: RNA
<213> ORGANISM: Homo sapiens

<400> SEQUENCE: 3

ccucccacac ccaaggcuug ca                                              22


<210> SEQ ID NO 4
<211> LENGTH: 22
<212> TYPE: RNA
<213> ORGANISM: Homo sapiens

<400> SEQUENCE: 4

uguaaacauc cucgacugga ag                                              22


<210> SEQ ID NO 5
<211> LENGTH: 22
<212> TYPE: RNA
<213> ORGANISM: Homo sapiens

<400> SEQUENCE: 5

uagcuuauca gacugauguu ga                                              22


<210> SEQ ID NO 6
<211> LENGTH: 21
<212> TYPE: RNA
<213> ORGANISM: Homo sapiens

<400> SEQUENCE: 6

uacaguacug ugauaacuga a                                               21


<210> SEQ ID NO 7
<211> LENGTH: 22
<212> TYPE: RNA
```

<213> ORGANISM: Homo sapiens

<400> SEQUENCE: 7
aauugcacgg uauccaucug ua 22

<210> SEQ ID NO 8
<211> LENGTH: 23
<212> TYPE: RNA
<213> ORGANISM: Homo sapiens

<400> SEQUENCE: 8
ugucugcccg caugccugcc ucu 23

<210> SEQ ID NO 9
<211> LENGTH: 23
<212> TYPE: RNA
<213> ORGANISM: Homo sapiens

<400> SEQUENCE: 9
caaagugcuc auagugcagg uag 23

<210> SEQ ID NO 10
<211> LENGTH: 22
<212> TYPE: RNA
<213> ORGANISM: Homo sapiens

<400> SEQUENCE: 10
cauugcacuu gucucggucu ga 22

<210> SEQ ID NO 11
<211> LENGTH: 22
<212> TYPE: RNA
<213> ORGANISM: Homo sapiens

<400> SEQUENCE: 11
uggagagaaa ggcaguuccu ga 22

<210> SEQ ID NO 12
<211> LENGTH: 21
<212> TYPE: RNA
<213> ORGANISM: Homo sapiens

<400> SEQUENCE: 12
aaaccguuac cauuacugag u 21

<210> SEQ ID NO 13
<211> LENGTH: 23
<212> TYPE: RNA
<213> ORGANISM: Homo sapiens

<400> SEQUENCE: 13
ugaggggcag agagcgagac uuu 23

<210> SEQ ID NO 14
<211> LENGTH: 22
<212> TYPE: RNA
<213> ORGANISM: Homo sapiens

<400> SEQUENCE: 14
aagcugccag uugaagaacu gu 22

<210> SEQ ID NO 15
<211> LENGTH: 22

<212> TYPE: RNA
<213> ORGANISM: Homo sapiens

<400> SEQUENCE: 15
uauugcacuc gucccggccu cc 22

<210> SEQ ID NO 16
<211> LENGTH: 22
<212> TYPE: RNA
<213> ORGANISM: Homo sapiens

<400> SEQUENCE: 16
uauugcacuu gucccggccu gu 22

<210> SEQ ID NO 17
<211> LENGTH: 21
<212> TYPE: RNA
<213> ORGANISM: Homo sapiens

<400> SEQUENCE: 17
cggggcagcu caguacagga u 21

<210> SEQ ID NO 18
<211> LENGTH: 23
<212> TYPE: RNA
<213> ORGANISM: Homo sapiens

<400> SEQUENCE: 18
ugugcaaauc caugcaaaac uga 23

<210> SEQ ID NO 19
<211> LENGTH: 82
<212> TYPE: RNA
<213> ORGANISM: Homo sapiens

<400> SEQUENCE: 19
gcuucgcucc ccuccgccuu cucuucccgg uucuucccgg agucgggaaa agcuggguug 60
agagggcgaa aaaggaugag gu 82

<210> SEQ ID NO 20
<211> LENGTH: 84
<212> TYPE: RNA
<213> ORGANISM: Homo sapiens

<400> SEQUENCE: 20
gucagaauaa ugucaaagug cuuacagugc agguagugau augugcaucu acugcaguga 60
aggcacuugu agcauuaugg ugac 84

<210> SEQ ID NO 21
<211> LENGTH: 91
<212> TYPE: RNA
<213> ORGANISM: Homo sapiens

<400> SEQUENCE: 21
cgacuugcuu ucucuccucc augccuugag uguaggaccg uuggcaucuu aauuacccuc 60
ccacacccaa ggcuugcaaa aaagcgagcc u 91

<210> SEQ ID NO 22
<211> LENGTH: 71
<212> TYPE: RNA
<213> ORGANISM: Homo sapiens

<400> SEQUENCE: 22
gcgacuguaa acauccucga cuggaagcug ugaagccaca gaugggcuuu cagucggaug 60
uuugcagcug c 71

<210> SEQ ID NO 23
<211> LENGTH: 72
<212> TYPE: RNA
<213> ORGANISM: Homo sapiens

<400> SEQUENCE: 23
ugucggguag cuuaucagac ugauguugac uguugaaucu cauggcaaca ccagucgaug 60
ggcugucuga ca 72

<210> SEQ ID NO 24
<211> LENGTH: 75
<212> TYPE: RNA
<213> ORGANISM: Homo sapiens

<400> SEQUENCE: 24
ugcccuggcu caguuaucac agugcugaug cugucuauuc uaaagguaca guacugugau 60
aacugaagga uggca 75

<210> SEQ ID NO 25
<211> LENGTH: 79
<212> TYPE: RNA
<213> ORGANISM: Homo sapiens

<400> SEQUENCE: 25
acuguccuuu uucgguuauc augguaccga ugcuguauau cugaaaggua caguacugug 60
auaacugaag aaugguggu 79

<210> SEQ ID NO 26
<211> LENGTH: 75
<212> TYPE: RNA
<213> ORGANISM: Homo sapiens

<400> SEQUENCE: 26
uguugucggg uggaucacga ugcaauuuug augaguauca uaggagaaaa auugcacggu 60
auccaucugu aaacc 75

<210> SEQ ID NO 27
<211> LENGTH: 95
<212> TYPE: RNA
<213> ORGANISM: Homo sapiens

<400> SEQUENCE: 27
ggucucugug uugggcgucu gucugcccgc augccugccu cucuguugcu cugaaggagg 60
caggggcugg gccugcagcu gccugggcag agcgg 95

<210> SEQ ID NO 28
<211> LENGTH: 69
<212> TYPE: RNA
<213> ORGANISM: Homo sapiens

<400> SEQUENCE: 28
aguaccaaag ugcucauagu gcagguaguu uuggcaugac ucuacuguag uaugggcacu 60
uccaguacu 69

<210> SEQ ID NO 29
<211> LENGTH: 84
<212> TYPE: RNA
<213> ORGANISM: Homo sapiens

<400> SEQUENCE: 29
ggccaguguu gagaggcgga gacuugggca auugcuggac gcugcccugg gcauugcacu 60
ugucucgguc ugacagugcc ggcc 84

<210> SEQ ID NO 30
<211> LENGTH: 82
<212> TYPE: RNA
<213> ORGANISM: Homo sapiens

<400> SEQUENCE: 30
agggggcgag ggauuggaga gaaaggcagu uccugauggu ccccuccca ggggcuggcu 60 uuccucuggu ccuucccucc ca 82

<210> SEQ ID NO 31
<211> LENGTH: 72
<212> TYPE: RNA
<213> ORGANISM: Homo sapiens

<400> SEQUENCE: 31
cuugggaaug gcaaggaaac cguuaccauu acugaguuua guaaugguaa ugguucucuu 60
gcuauaccca ga 72

<210> SEQ ID NO 32
<211> LENGTH: 94
<212> TYPE: RNA
<213> ORGANISM: Homo sapiens

<400> SEQUENCE: 32
auaaaggaag uuaggcugag gggcagagag cgagacuuuu cuauuuucca aaagcucggu 60
cugaggcccc ucagucuugc uuccuaaccc gcgc 94

<210> SEQ ID NO 33
<211> LENGTH: 85
<212> TYPE: RNA
<213> ORGANISM: Homo sapiens

<400> SEQUENCE: 33
ggcugagccg caguaguucu ucaguggcaa gcuuuauguc cugacccagc uaaagcugcc 60
aguugaagaa cuguugcccu cugcc 85

<210> SEQ ID NO 34
<211> LENGTH: 96
<212> TYPE: RNA
<213> ORGANISM: Homo sapiens

<400> SEQUENCE: 34
cgggccccgg gcgggcggga gggacgggac gcggugcagu guuguuuuuu cccccgccaa 60
uauugcacuc gucccggccu ccggcccccc cggccc 96

<210> SEQ ID NO 35
<211> LENGTH: 78
<212> TYPE: RNA
<213> ORGANISM: Homo sapiens

<400> SEQUENCE: 35
cuuucuacac agguugggau cgguugcaau gcuguguuuc uguaugguau ugcacuuguc 60
ccggccuguu gaguuugg 78

<210> SEQ ID NO 36
<211> LENGTH: 75
<212> TYPE: RNA
<213> ORGANISM: Homo sapiens

<400> SEQUENCE: 36
ucaucccugg guggggauuu guugcauuac uuguguucua uauaaaguau ugcacuuguc 60
ccggccugug gaaga 75

<210> SEQ ID NO 37
<211> LENGTH: 68
<212> TYPE: RNA
<213> ORGANISM: Homo sapiens

<400> SEQUENCE: 37
gcauccugua cugagcugcc ccgaggcccu ucaugcugcc cagcucgggg cagcucagua 60
caggauac 68

<210> SEQ ID NO 38
<211> LENGTH: 87
<212> TYPE: RNA
<213> ORGANISM: Homo sapiens

<400> SEQUENCE: 38
cacuguucua ugguuaguuu ugcagguuug cauccagcug ugugauauuc ugcugugcaa 60
auccaugcaa aacugacugu gguagug 87

<210> SEQ ID NO 39
<211> LENGTH: 96
<212> TYPE: RNA
<213> ORGANISM: Homo sapiens

<400> SEQUENCE: 39
acauugcuac uuacaauuag uuuugcaggu uugcauuuca gcguauauau guauaugugg 60
cugugcaaau ccaugcaaaa cugauuguga uaaugu 96

<210> SEQ ID NO 40
<211> LENGTH: 22
<212> TYPE: RNA
<213> ORGANISM: Homo sapiens

<400> SEQUENCE: 40
uucaaguaau ccaggauagg cu 22

<210> SEQ ID NO 41
<211> LENGTH: 21
<212> TYPE: RNA
<213> ORGANISM: Homo sapiens

<400> SEQUENCE: 41
gugcauugua guugcauugc a 21

<210> SEQ ID NO 42
<211> LENGTH: 23
<212> TYPE: RNA
<213> ORGANISM: Homo sapiens

<400> SEQUENCE: 42

```
cccaguguuu agacuaucug uuc                                              23


<210> SEQ ID NO 43
<211> LENGTH: 21
<212> TYPE: RNA
<213> ORGANISM: Homo sapiens

<400> SEQUENCE: 43

uucacagugg cuaaguucug c                                                21


<210> SEQ ID NO 44
<211> LENGTH: 77
<212> TYPE: RNA
<213> ORGANISM: Homo sapiens

<400> SEQUENCE: 44

guggccucgu ucaaguaauc caggauaggc ugugcagguc ccaaugggcc uauucuuggu      60

uacuugcacg gggacgc                                                     77


<210> SEQ ID NO 45
<211> LENGTH: 84
<212> TYPE: RNA
<213> ORGANISM: Homo sapiens

<400> SEQUENCE: 45

ggcuguggcu ggauucaagu aauccaggau aggcuguuuc caucugugag gccuauucuu      60

gauuacuugu uucuggaggc agcu                                             84


<210> SEQ ID NO 46
<211> LENGTH: 69
<212> TYPE: RNA
<213> ORGANISM: Homo sapiens

<400> SEQUENCE: 46

cuguggugca uuguaguugc auugcauguu cugguguac ccaugcaaug uuuccacagu       60

gcaucacag                                                              69


<210> SEQ ID NO 47
<211> LENGTH: 110
<212> TYPE: RNA
<213> ORGANISM: Homo sapiens

<400> SEQUENCE: 47

ccagaggaca ccuccacucc gucuacccag uguuuagacu aucuguucag gacucccaaa      60

uuguacagua gucugcacau ugguuaggcu gggcugggguu agacccucgg               110


<210> SEQ ID NO 48
<211> LENGTH: 97
<212> TYPE: RNA
<213> ORGANISM: Homo sapiens

<400> SEQUENCE: 48

accucucuaa caaggugcag agcuuagcug auuggugaac agugauuggu uuccgcuuug      60

uucacagugg cuaaguucug caccugaaga gaaggug                               97


<210> SEQ ID NO 49
<211> LENGTH: 28
<212> TYPE: DNA
<213> ORGANISM: artificial sequence
<220> FEATURE:
```

<223> OTHER INFORMATION: Synthetic

<400> SEQUENCE: 49
cagtcatttg ggaaaagctg ggttgaga 28

<210> SEQ ID NO 50
<211> LENGTH: 28
<212> TYPE: DNA
<213> ORGANISM: artificial sequence
<220> FEATURE:
<223> OTHER INFORMATION: Synthetic

<400> SEQUENCE: 50
cagtcatttg gctacagtac tgtgataa 28

<210> SEQ ID NO 51
<211> LENGTH: 28
<212> TYPE: DNA
<213> ORGANISM: artificial sequence
<220> FEATURE:
<223> OTHER INFORMATION: Synthetic

<400> SEQUENCE: 51
cagtcatttg gcactgcagt gaaggcac 28

<210> SEQ ID NO 52
<211> LENGTH: 28
<212> TYPE: DNA
<213> ORGANISM: artificial sequence
<220> FEATURE:
<223> OTHER INFORMATION: Synthetic

<400> SEQUENCE: 52
cagtcatttg gctggagaga aaggcagt 28

<210> SEQ ID NO 53
<211> LENGTH: 28
<212> TYPE: DNA
<213> ORGANISM: artificial sequence
<220> FEATURE:
<223> OTHER INFORMATION: Synthetic

<400> SEQUENCE: 53
cagtcatttg gctgtgcaaa tccatgca 28

<210> SEQ ID NO 54
<211> LENGTH: 28
<212> TYPE: DNA
<213> ORGANISM: artificial sequence
<220> FEATURE:
<223> OTHER INFORMATION: Synthetic

<400> SEQUENCE: 54
cagtcatttg gccaaagtgc tcatagtg 28

<210> SEQ ID NO 55
<211> LENGTH: 28
<212> TYPE: DNA
<213> ORGANISM: artificial sequence
<220> FEATURE:
<223> OTHER INFORMATION: Synthetic

<400> SEQUENCE: 55
cagtcatttg ggtgtaaaca tcctcgac 28

<210> SEQ ID NO 56
<211> LENGTH: 28
<212> TYPE: DNA
<213> ORGANISM: artificial sequence
<220> FEATURE:
<223> OTHER INFORMATION: Synthetic

<400> SEQUENCE: 56
cagtcatttg gcaattgcac ggtatcca 28

<210> SEQ ID NO 57
<211> LENGTH: 28
<212> TYPE: DNA
<213> ORGANISM: artificial sequence
<220> FEATURE:
<223> OTHER INFORMATION: Synthetic

<400> SEQUENCE: 57
cagtcatttg ggaaaccgtt accattac 28

<210> SEQ ID NO 58
<211> LENGTH: 28
<212> TYPE: DNA
<213> ORGANISM: artificial sequence
<220> FEATURE:
<223> OTHER INFORMATION: Synthetic

<400> SEQUENCE: 58
cagtcatttg gctattgcac ttgtcccg 28

<210> SEQ ID NO 59
<211> LENGTH: 28
<212> TYPE: DNA
<213> ORGANISM: artificial sequence
<220> FEATURE:
<223> OTHER INFORMATION: Synthetic

<400> SEQUENCE: 59
cagtcatttg ggtattgcac tcgtcccg 28

<210> SEQ ID NO 60
<211> LENGTH: 28
<212> TYPE: DNA
<213> ORGANISM: artificial sequence
<220> FEATURE:
<223> OTHER INFORMATION: Synthetic

<400> SEQUENCE: 60
cagtcatttg gctagcttat cagactga 28

<210> SEQ ID NO 61
<211> LENGTH: 28
<212> TYPE: DNA
<213> ORGANISM: artificial sequence
<220> FEATURE:
<223> OTHER INFORMATION: Synthetic

<400> SEQUENCE: 61
cagtcatttg gcaagctgcc agttgaag 28

<210> SEQ ID NO 62
<211> LENGTH: 28
<212> TYPE: DNA
<213> ORGANISM: artificial sequence
<220> FEATURE:
<223> OTHER INFORMATION: Synthetic

<400> SEQUENCE: 62
cagtcatttg gccattgcac ttgtctcg 28

<210> SEQ ID NO 63
<211> LENGTH: 28
<212> TYPE: DNA
<213> ORGANISM: artificial sequence
<220> FEATURE:
<223> OTHER INFORMATION: Synthetic

<400> SEQUENCE: 63
cagtcatttg gctgtctgcc cgcatgcc 28

<210> SEQ ID NO 64
<211> LENGTH: 28
<212> TYPE: DNA
<213> ORGANISM: artificial sequence
<220> FEATURE:
<223> OTHER INFORMATION: Synthetic

<400> SEQUENCE: 64
cagtcatttg gctgaggggc agagagcg 28

<210> SEQ ID NO 65
<211> LENGTH: 21
<212> TYPE: DNA
<213> ORGANISM: artificial sequence
<220> FEATURE:
<223> OTHER INFORMATION: Synthetic

<400> SEQUENCE: 65
cggggcagct cagtacagga t 21

<210> SEQ ID NO 66
<211> LENGTH: 22
<212> TYPE: DNA
<213> ORGANISM: artificial sequence
<220> FEATURE:
<223> OTHER INFORMATION: Synthetic

<400> SEQUENCE: 66
cctcccacac ccaaggcttg ca 22

<210> SEQ ID NO 67
<211> LENGTH: 23
<212> TYPE: DNA
<213> ORGANISM: artificial sequence
<220> FEATURE:
<223> OTHER INFORMATION: Synthetic

<400> SEQUENCE: 67
ccgttttttt tttttcgccc tct 23

<210> SEQ ID NO 68
<211> LENGTH: 23
<212> TYPE: DNA
<213> ORGANISM: artificial sequence
<220> FEATURE:
<223> OTHER INFORMATION: Synthetic

<400> SEQUENCE: 68
ccgttttttt tttttcagtt atc 23

<210> SEQ ID NO 69
<211> LENGTH: 25

<212> TYPE: DNA
<213> ORGANISM: artificial sequence
<220> FEATURE:
<223> OTHER INFORMATION: Synthetic

<400> SEQUENCE: 69
atccgttttt tttttttcta caagt 25

<210> SEQ ID NO 70
<211> LENGTH: 22
<212> TYPE: DNA
<213> ORGANISM: artificial sequence
<220> FEATURE:
<223> OTHER INFORMATION: Synthetic

<400> SEQUENCE: 70
cgtttttttt ttttcaggaa ct 22

<210> SEQ ID NO 71
<211> LENGTH: 22
<212> TYPE: DNA
<213> ORGANISM: artificial sequence
<220> FEATURE:
<223> OTHER INFORMATION: Synthetic

<400> SEQUENCE: 71
cgtttttttt ttttcagttt tg 22

<210> SEQ ID NO 72
<211> LENGTH: 23
<212> TYPE: DNA
<213> ORGANISM: artificial sequence
<220> FEATURE:
<223> OTHER INFORMATION: Synthetic

<400> SEQUENCE: 72
ccgttttttt tttttctacc tgc 23

<210> SEQ ID NO 73
<211> LENGTH: 23
<212> TYPE: DNA
<213> ORGANISM: artificial sequence
<220> FEATURE:
<223> OTHER INFORMATION: Synthetic

<400> SEQUENCE: 73
ccgttttttt tttttcttcc agt 23

<210> SEQ ID NO 74
<211> LENGTH: 23
<212> TYPE: DNA
<213> ORGANISM: artificial sequence
<220> FEATURE:
<223> OTHER INFORMATION: Synthetic

<400> SEQUENCE: 74
ccgttttttt tttttacaga tgg 23

<210> SEQ ID NO 75
<211> LENGTH: 24
<212> TYPE: DNA
<213> ORGANISM: artificial sequence
<220> FEATURE:
<223> OTHER INFORMATION: Synthetic

<400> SEQUENCE: 75

```
tccgtttttt ttttttactc agta                                              24


<210> SEQ ID NO 76
<211> LENGTH: 22
<212> TYPE: DNA
<213> ORGANISM: artificial sequence
<220> FEATURE:
<223> OTHER INFORMATION: Synthetic

<400> SEQUENCE: 76

cgtttttttt ttttacaggc cg                                                22


<210> SEQ ID NO 77
<211> LENGTH: 22
<212> TYPE: DNA
<213> ORGANISM: artificial sequence
<220> FEATURE:
<223> OTHER INFORMATION: Synthetic

<400> SEQUENCE: 77

cgtttttttt ttttggaggc cg                                                22


<210> SEQ ID NO 78
<211> LENGTH: 23
<212> TYPE: DNA
<213> ORGANISM: artificial sequence
<220> FEATURE:
<223> OTHER INFORMATION: Synthetic

<400> SEQUENCE: 78

ccgttttttt tttttcaaca tca                                               23


<210> SEQ ID NO 79
<211> LENGTH: 23
<212> TYPE: DNA
<213> ORGANISM: artificial sequence
<220> FEATURE:
<223> OTHER INFORMATION: Synthetic

<400> SEQUENCE: 79

ccgttttttt tttttacagt tct                                               23


<210> SEQ ID NO 80
<211> LENGTH: 23
<212> TYPE: DNA
<213> ORGANISM: artificial sequence
<220> FEATURE:
<223> OTHER INFORMATION: Synthetic

<400> SEQUENCE: 80

ccgttttttt tttttcagac cga                                               23


<210> SEQ ID NO 81
<211> LENGTH: 23
<212> TYPE: DNA
<213> ORGANISM: artificial sequence
<220> FEATURE:
<223> OTHER INFORMATION: Synthetic

<400> SEQUENCE: 81

ccgttttttt tttttagagg cag                                               23


<210> SEQ ID NO 82
<211> LENGTH: 23
<212> TYPE: DNA
<213> ORGANISM: artificial sequence
```

<220> FEATURE:
<223> OTHER INFORMATION: Synthetic

<400> SEQUENCE: 82
ccgttttttt tttttaaagt ctc 23

<210> SEQ ID NO 83
<211> LENGTH: 18
<212> TYPE: DNA
<213> ORGANISM: artificial sequence
<220> FEATURE:
<223> OTHER INFORMATION: Synthetic

<400> SEQUENCE: 83
aaaaccgata gtgagtcg 18

<210> SEQ ID NO 84
<211> LENGTH: 18
<212> TYPE: DNA
<213> ORGANISM: artificial sequence
<220> FEATURE:
<223> OTHER INFORMATION: Synthetic

<400> SEQUENCE: 84
aaaaccgata gtgagtcg 18

<210> SEQ ID NO 85
<211> LENGTH: 22
<212> TYPE: DNA
<213> ORGANISM: artificial sequence
<220> FEATURE:
<223> OTHER INFORMATION: Synthetic

<400> SEQUENCE: 85
gcgagcacag aattaatacg ac 22

<210> SEQ ID NO 86
<211> LENGTH: 28
<212> TYPE: DNA
<213> ORGANISM: artificial sequence
<220> FEATURE:
<223> OTHER INFORMATION: Synthetic

<400> SEQUENCE: 86
cagtcatttg gcttcaagta atccagga 28

<210> SEQ ID NO 87
<211> LENGTH: 28
<212> TYPE: DNA
<213> ORGANISM: artificial sequence
<220> FEATURE:
<223> OTHER INFORMATION: Synthetic

<400> SEQUENCE: 87
cagtcatttg ggttcacagt ggctaagt 28

<210> SEQ ID NO 88
<211> LENGTH: 28
<212> TYPE: DNA
<213> ORGANISM: artificial sequence
<220> FEATURE:
<223> OTHER INFORMATION: Synthetic

<400> SEQUENCE: 88
cagtcatttg gccccagtgt ttagacta 28

<210> SEQ ID NO 89
<211> LENGTH: 28
<212> TYPE: DNA
<213> ORGANISM: artificial sequence
<220> FEATURE:
<223> OTHER INFORMATION: Synthetic

<400> SEQUENCE: 89
cagtcatttg gcgtgcattg tagttgca 28

<210> SEQ ID NO 90
<211> LENGTH: 23
<212> TYPE: DNA
<213> ORGANISM: artificial sequence
<220> FEATURE:
<223> OTHER INFORMATION: Synthetic

<400> SEQUENCE: 90
ccgttttttt tttttagcct atc 23

<210> SEQ ID NO 91
<211> LENGTH: 22
<212> TYPE: DNA
<213> ORGANISM: artificial sequence
<220> FEATURE:
<223> OTHER INFORMATION: Synthetic

<400> SEQUENCE: 91
cgtttttttt ttttgcagaa ct 22

<210> SEQ ID NO 92
<211> LENGTH: 23
<212> TYPE: DNA
<213> ORGANISM: artificial sequence
<220> FEATURE:
<223> OTHER INFORMATION: Synthetic

<400> SEQUENCE: 92
ccgttttttt tttttgaaca gat 23

<210> SEQ ID NO 93
<211> LENGTH: 23
<212> TYPE: DNA
<213> ORGANISM: artificial sequence
<220> FEATURE:
<223> OTHER INFORMATION: Synthetic

<400> SEQUENCE: 93
ccgttttttt tttttgcaat gca 23

<210> SEQ ID NO 94
<211> LENGTH: 22
<212> TYPE: RNA
<213> ORGANISM: Homo sapiens

<400> SEQUENCE: 94
uagcaccauu ugaaaucggu ua 22

<210> SEQ ID NO 95
<211> LENGTH: 22
<212> TYPE: RNA
<213> ORGANISM: Homo sapiens

<400> SEQUENCE: 95
uguaaacauc cccgacugga ag 22

<210> SEQ ID NO 96
<211> LENGTH: 21
<212> TYPE: RNA
<213> ORGANISM: Homo sapiens

<400> SEQUENCE: 96
uaccacaggg uagaaccacg g 21

<210> SEQ ID NO 97
<211> LENGTH: 22
<212> TYPE: RNA
<213> ORGANISM: Homo sapiens

<400> SEQUENCE: 97
ugagguagua gguugugugg uu 22

<210> SEQ ID NO 98
<211> LENGTH: 21
<212> TYPE: RNA
<213> ORGANISM: Homo sapiens

<400> SEQUENCE: 98
gccccugggc cuauccuaga a 21

<210> SEQ ID NO 99
<211> LENGTH: 22
<212> TYPE: RNA
<213> ORGANISM: Homo sapiens

<400> SEQUENCE: 99
ugcggggcua gggcuaacag ca 22

<210> SEQ ID NO 100
<211> LENGTH: 22
<212> TYPE: RNA
<213> ORGANISM: Homo sapiens

<400> SEQUENCE: 100
aaggagcuca cagucuauug ag 22

<210> SEQ ID NO 101
<211> LENGTH: 22
<212> TYPE: RNA
<213> ORGANISM: Homo sapiens

<400> SEQUENCE: 101
cacgcucaug cacacaccca ca 22

<210> SEQ ID NO 102
<211> LENGTH: 22
<212> TYPE: RNA
<213> ORGANISM: Homo sapiens

<400> SEQUENCE: 102
ugucaguuug ucaaauaccc ca 22

<210> SEQ ID NO 103
<211> LENGTH: 23
<212> TYPE: RNA
<213> ORGANISM: Homo sapiens

<400> SEQUENCE: 103
uguaguguuu ccuacuuuau gga 23

<210> SEQ ID NO 104
<211> LENGTH: 21
<212> TYPE: RNA
<213> ORGANISM: Homo sapiens

<400> SEQUENCE: 104
uucacagugg cuaaguuccg c 21

<210> SEQ ID NO 105
<211> LENGTH: 23
<212> TYPE: RNA
<213> ORGANISM: Homo sapiens

<400> SEQUENCE: 105
caacggaauc ccaaaagcag cug 23

<210> SEQ ID NO 106
<211> LENGTH: 23
<212> TYPE: RNA
<213> ORGANISM: Homo sapiens

<400> SEQUENCE: 106
ucaagagcaa uaacgaaaaa ugu 23

<210> SEQ ID NO 107
<211> LENGTH: 22
<212> TYPE: RNA
<213> ORGANISM: Homo sapiens

<400> SEQUENCE: 107
uggcucaguu cagcaggaac ag 22

<210> SEQ ID NO 108
<211> LENGTH: 21
<212> TYPE: RNA
<213> ORGANISM: Homo sapiens

<400> SEQUENCE: 108
ucgaggagcu cacagucuag u 21

<210> SEQ ID NO 109
<211> LENGTH: 22
<212> TYPE: RNA
<213> ORGANISM: Homo sapiens

<400> SEQUENCE: 109
ucguaccgug aguaauaaug cg 22

<210> SEQ ID NO 110
<211> LENGTH: 24
<212> TYPE: RNA
<213> ORGANISM: Homo sapiens

<400> SEQUENCE: 110
ucccugagac ccuuuaaccu guga 24

<210> SEQ ID NO 111
<211> LENGTH: 22
<212> TYPE: RNA
<213> ORGANISM: Homo sapiens

<400> SEQUENCE: 111
ugagguagua gauuguauag uu 22

<210> SEQ ID NO 112
<211> LENGTH: 21
<212> TYPE: RNA
<213> ORGANISM: Homo sapiens

<400> SEQUENCE: 112
aucacauugc cagggauuuc c 21

<210> SEQ ID NO 113
<211> LENGTH: 22
<212> TYPE: RNA
<213> ORGANISM: Homo sapiens

<400> SEQUENCE: 113
cuuucagucg gauguuuaca gc 22

<210> SEQ ID NO 114
<211> LENGTH: 20
<212> TYPE: RNA
<213> ORGANISM: Homo sapiens

<400> SEQUENCE: 114
ccucugggcc cuuccuccag 20

<210> SEQ ID NO 115
<211> LENGTH: 22
<212> TYPE: RNA
<213> ORGANISM: Homo sapiens

<400> SEQUENCE: 115
cacccguaga accgaccuug cg 22

<210> SEQ ID NO 116
<211> LENGTH: 22
<212> TYPE: RNA
<213> ORGANISM: Homo sapiens

<400> SEQUENCE: 116
ucuccgggga ggcaggaaug ug 22

<210> SEQ ID NO 117
<211> LENGTH: 22
<212> TYPE: RNA
<213> ORGANISM: Homo sapiens

<400> SEQUENCE: 117
cucccacugc uucacuugac ua 22

<210> SEQ ID NO 118
<211> LENGTH: 18
<212> TYPE: RNA
<213> ORGANISM: Homo sapiens

<400> SEQUENCE: 118
acacucaaac ugcugaca 18

<210> SEQ ID NO 119
<211> LENGTH: 88
<212> TYPE: RNA
<213> ORGANISM: Homo sapiens

<400> SEQUENCE: 119
aucucuuaca caggcugacc gauuucuccu gguguucaga gucuguuuuu gucuagcacc 60
auuugaaauc gguuaugaug uaggggga 88

<210> SEQ ID NO 120
<211> LENGTH: 70
<212> TYPE: RNA
<213> ORGANISM: Homo sapiens

<400> SEQUENCE: 120
guuguuguaa acauccccga cuggaagcug uaagacacag cuaagcuuuc agucagaugu 60
uugcugcuac 70

<210> SEQ ID NO 121
<211> LENGTH: 100
<212> TYPE: RNA
<213> ORGANISM: Homo sapiens

<400> SEQUENCE: 121
ugugucucuc ucuguguccu gccagugguu uuacccuaug guagguuacg ucaugcuguu 60
cuaccacagg guagaaccac ggacaggaua ccggggcacc 100

<210> SEQ ID NO 122
<211> LENGTH: 83
<212> TYPE: RNA
<213> ORGANISM: Homo sapiens

<400> SEQUENCE: 122
cggggugagg uaguagguug ugugguuuca gggcagugau guugccccuc ggaagauaac 60
uauacaaccu acugccuucc cug 83

<210> SEQ ID NO 123
<211> LENGTH: 94
<212> TYPE: RNA
<213> ORGANISM: Homo sapiens

<400> SEQUENCE: 123
gaguuugguu uuguuugggu uuguucuagg uaugguccca gggaucccag aucaaaccag 60
gccccugggc cuauccuaga accaaccuaa gcuc 94

<210> SEQ ID NO 124
<211> LENGTH: 98
<212> TYPE: RNA
<213> ORGANISM: Homo sapiens

<400> SEQUENCE: 124
uugggcaagg ugcggggcua gggcuaacag cagucuuacu gaagguuucc uggaaaccac 60
gcacaugcug uugccacuaa ccucaaccuu acucgguc 98

<210> SEQ ID NO 125
<211> LENGTH: 86
<212> TYPE: RNA
<213> ORGANISM: Homo sapiens

<400> SEQUENCE: 125
gguccuugcc cucaaggagc ucacagucua uugaguuacc uuucugacuu ucccacuaga 60
uugugagcuc cuggagggca ggcacu 86

<210> SEQ ID NO 126
<211> LENGTH: 96
<212> TYPE: RNA
<213> ORGANISM: Homo sapiens

<400> SEQUENCE: 126
gggaccugcg ugggugcggg cgugugagug ugugugugug agugugugcu gcuccggguc 60
cacgcucaug cacacaccca cacgcccaca cucagg 96

<210> SEQ ID NO 127
<211> LENGTH: 110
<212> TYPE: RNA
<213> ORGANISM: Homo sapiens

<400> SEQUENCE: 127
ccuggccucc ugcagugcca cgcuccgugu auuugacaag cugaguugga cacuccaugu 60
gguagagugu caguuuguca aauaccccaa gugcggcaca ugcuuaccag 110

<210> SEQ ID NO 128
<211> LENGTH: 87
<212> TYPE: RNA
<213> ORGANISM: Homo sapiens

<400> SEQUENCE: 128
gacagugcag ucacccauaa aguagaaagc acuacuaaca gcacuggagg guguaguguu 60
uccuacuuua uggaugagug uacugug 87

<210> SEQ ID NO 129
<211> LENGTH: 78
<212> TYPE: RNA
<213> ORGANISM: Homo sapiens

<400> SEQUENCE: 129
cugaggagca gggcuuagcu gcuugugagc aggguccaca ccaagucgug uucacagugg 60
cuaaguuccg cccccag 78

<210> SEQ ID NO 130
<211> LENGTH: 92
<212> TYPE: RNA
<213> ORGANISM: Homo sapiens

<400> SEQUENCE: 130
cggcuggaca gcgggcaacg gaaucccaaa agcagcuguu gucuccagag cauuccagcu 60
gcgcuuggau uucguccccu gcucuccugc cu 92

<210> SEQ ID NO 131
<211> LENGTH: 94
<212> TYPE: RNA
<213> ORGANISM: Homo sapiens

<400> SEQUENCE: 131
uguuuugagc gggggucaag agcaauaacg aaaaauguuu gucauaaacc guuuuucauu 60
auugcuccug accuccucuc auuugcuaua uuca 94

<210> SEQ ID NO 132
<211> LENGTH: 68
<212> TYPE: RNA
<213> ORGANISM: Homo sapiens

<400> SEQUENCE: 132

-continued cuccggugcc uacugagcug auaucaguuc ucauuuuaca cacuggcuca guucagcagg 60
aacaggag 68

<210> SEQ ID NO 133
<211> LENGTH: 73
<212> TYPE: RNA
<213> ORGANISM: Homo sapiens

<400> SEQUENCE: 133
cucugccucc cgugccuacu gagcugaaac acaguugguu uguguacacu ggcucaguuc 60
agcaggaaca ggg 73

<210> SEQ ID NO 134
<211> LENGTH: 90
<212> TYPE: RNA
<213> ORGANISM: Homo sapiens

<400> SEQUENCE: 134
uuuccugccc ucgaggagcu cacagucuag uaugucucau ccccuacuag acugaagcuc 60
cuugaggaca gggaugguca uacucaccuc 90

<210> SEQ ID NO 135
<211> LENGTH: 85
<212> TYPE: RNA
<213> ORGANISM: Homo sapiens

<400> SEQUENCE: 135
cgcuggcgac gggacauuau uacuuuuggu acgcgcugug acacuucaaa cucguaccgu 60
gaguaauaau gcgccgucca cggca 85

<210> SEQ ID NO 136
<211> LENGTH: 86
<212> TYPE: RNA
<213> ORGANISM: Homo sapiens

<400> SEQUENCE: 136
ugccagucuc uaggucccug agacccuuua accugugagg acauccaggg ucacagguga 60
gguucuuggg agccuggcgu cuggcc 86

<210> SEQ ID NO 137
<211> LENGTH: 87
<212> TYPE: RNA
<213> ORGANISM: Homo sapiens

<400> SEQUENCE: 137
ucagagugag guaguagauu guauaguugu gggguaguga uuuuacccug uucaggagau 60
aacuauacaa ucuauugccu ucccuga 87

<210> SEQ ID NO 138
<211> LENGTH: 83
<212> TYPE: RNA
<213> ORGANISM: Homo sapiens

<400> SEQUENCE: 138
ugugggauga gguaguagau uguauaguuu uagggucaua ccccaucuug gagauaacua 60
uacagucuac ugucuuuccc acg 83

<210> SEQ ID NO 139
<211> LENGTH: 73

<212> TYPE: RNA
<213> ORGANISM: Homo sapiens

<400> SEQUENCE: 139
ggccggcugg gguuccuggg gaugggauuu gcuuccuguc acaaaucaca uugccaggga 60
uuuccaaccg acc 73

<210> SEQ ID NO 140
<211> LENGTH: 92
<212> TYPE: RNA
<213> ORGANISM: Homo sapiens

<400> SEQUENCE: 140
gggcagucuu ugcuacugua aacauccuug acuggaagcu guaaggugu cagaggagcu 60 uucagucgga uguuuacagc ggcaggcugc ca 92

<210> SEQ ID NO 141
<211> LENGTH: 95
<212> TYPE: RNA
<213> ORGANISM: Homo sapiens

<400> SEQUENCE: 141
cucaucuguc uguugggcug gaggcagggc cuuugugaag gcggguggug cucagaucgc 60
cucugggccc uuccuccagc cccgaggcgg auuca 95

<210> SEQ ID NO 142
<211> LENGTH: 70
<212> TYPE: RNA
<213> ORGANISM: Homo sapiens

<400> SEQUENCE: 142
ggcacccacc cguagaaccg accuugcggg gccuucgccg cacacaagcu cgugucugug 60
gguccguguc 70

<210> SEQ ID NO 143
<211> LENGTH: 94
<212> TYPE: RNA
<213> ORGANISM: Homo sapiens

<400> SEQUENCE: 143
ccaagccauu gagcgcugca uucccggccc ccuggcgacg gcccuggcca cggccaucuc 60
cggggaggca ggaauguggc gggcggggcu cugg 94

<210> SEQ ID NO 144
<211> LENGTH: 100
<212> TYPE: RNA
<213> ORGANISM: Homo sapiens

<400> SEQUENCE: 144
gugauccaca cucaaacugc ugacaacaua aaaccuuugu ccuuagaagu cugaauuuca 60
aaauuuuuaa aacauaauga auguuguuau gugaggccgc 100

<210> SEQ ID NO 145
<211> LENGTH: 130
<212> TYPE: RNA
<213> ORGANISM: Homo sapiens

<400> SEQUENCE: 145
cuaguggagg uacugugcuu uguguguugg aggaugaaag uacggaguga uccaucggcu 60
aagugucuug ucacaaugcu gacacucaaa cugcugacag cacacguuuu ucacaguacu 120
uacgccccag 130

<210> SEQ ID NO 146
<211> LENGTH: 76
<212> TYPE: RNA
<213> ORGANISM: Homo sapiens

<400> SEQUENCE: 146
ucuuuacucc cacugcuuca cuugacuagc cuuuaaaaaa gaaaggcuug guuugaugaa 60
ugggugagag aaaagg 76

<210> SEQ ID NO 147
<211> LENGTH: 28
<212> TYPE: DNA
<213> ORGANISM: artificial sequence
<220> FEATURE:
<223> OTHER INFORMATION: Synthetic

<400> SEQUENCE: 147
cagtcatttg gctgaggtag taggttgt 28

<210> SEQ ID NO 148
<211> LENGTH: 28
<212> TYPE: DNA
<213> ORGANISM: artificial sequence
<220> FEATURE:
<223> OTHER INFORMATION: Synthetic

<400> SEQUENCE: 148
cagtcatttg ggtgaggtag tagattgt 28

<210> SEQ ID NO 149
<211> LENGTH: 28
<212> TYPE: DNA
<213> ORGANISM: artificial sequence
<220> FEATURE:
<223> OTHER INFORMATION: Synthetic

<400> SEQUENCE: 149
cagtcatttg gctccctgag accctttta 28

<210> SEQ ID NO 150
<211> LENGTH: 28
<212> TYPE: DNA
<213> ORGANISM: artificial sequence
<220> FEATURE:
<223> OTHER INFORMATION: Synthetic

<400> SEQUENCE: 150
cagtcatttg ggtcgtaccg tgagtaat 28

<210> SEQ ID NO 151
<211> LENGTH: 28
<212> TYPE: DNA
<213> ORGANISM: artificial sequence
<220> FEATURE:
<223> OTHER INFORMATION: Synthetic

<400> SEQUENCE: 151
cagtcatttg gctaccacag ggtagaac 28

<210> SEQ ID NO 152
<211> LENGTH: 28

<212> TYPE: DNA
<213> ORGANISM: artificial sequence
<220> FEATURE:
<223> OTHER INFORMATION: Synthetic

<400> SEQUENCE: 152
cagtcatttg ggtgtagtgt ttcctact 28

<210> SEQ ID NO 153
<211> LENGTH: 28
<212> TYPE: DNA
<213> ORGANISM: artificial sequence
<220> FEATURE:
<223> OTHER INFORMATION: Synthetic

<400> SEQUENCE: 153
cagtcatttg ggtcgaggag ctcacagt 28

<210> SEQ ID NO 154
<211> LENGTH: 28
<212> TYPE: DNA
<213> ORGANISM: artificial sequence
<220> FEATURE:
<223> OTHER INFORMATION: Synthetic

<400> SEQUENCE: 154
cagtcatttg ggcaacggaa tcccaaaa 28

<210> SEQ ID NO 155
<211> LENGTH: 28
<212> TYPE: DNA
<213> ORGANISM: artificial sequence
<220> FEATURE:
<223> OTHER INFORMATION: Synthetic

<400> SEQUENCE: 155
cagtcatttg gctgtcagtt tgtcaaat 28

<210> SEQ ID NO 156
<211> LENGTH: 28
<212> TYPE: DNA
<213> ORGANISM: artificial sequence
<220> FEATURE:
<223> OTHER INFORMATION: Synthetic

<400> SEQUENCE: 156
cagtcatttg gcatcacatt gccaggga 28

<210> SEQ ID NO 157
<211> LENGTH: 28
<212> TYPE: DNA
<213> ORGANISM: artificial sequence
<220> FEATURE:
<223> OTHER INFORMATION: Synthetic

<400> SEQUENCE: 157
cagtcatttg gctggctcag ttcagcag 28

<210> SEQ ID NO 158
<211> LENGTH: 28
<212> TYPE: DNA
<213> ORGANISM: artificial sequence
<220> FEATURE:
<223> OTHER INFORMATION: Synthetic

<400> SEQUENCE: 158
cagtcatttg gcttcacagt ggctaagt 28

<210> SEQ ID NO 159
<211> LENGTH: 28
<212> TYPE: DNA
<213> ORGANISM: artificial sequence
<220> FEATURE:
<223> OTHER INFORMATION: Synthetic

<400> SEQUENCE: 159
cagtcatttg gcaaggagct cacagtct 28

<210> SEQ ID NO 160
<211> LENGTH: 28
<212> TYPE: DNA
<213> ORGANISM: artificial sequence
<220> FEATURE:
<223> OTHER INFORMATION: Synthetic

<400> SEQUENCE: 160
cagtcatttg gctagcacca tttgaaat 28

<210> SEQ ID NO 161
<211> LENGTH: 28
<212> TYPE: DNA
<213> ORGANISM: artificial sequence
<220> FEATURE:
<223> OTHER INFORMATION: Synthetic

<400> SEQUENCE: 161
cagtcatttg ggtgtaaaca tccccgac 28

<210> SEQ ID NO 162
<211> LENGTH: 28
<212> TYPE: DNA
<213> ORGANISM: artificial sequence
<220> FEATURE:
<223> OTHER INFORMATION: Synthetic

<400> SEQUENCE: 162
cagtcatttg gcctttcagt cggatgtt 28

<210> SEQ ID NO 163
<211> LENGTH: 28
<212> TYPE: DNA
<213> ORGANISM: artificial sequence
<220> FEATURE:
<223> OTHER INFORMATION: Synthetic

<400> SEQUENCE: 163
cagtcatttg gccctctggg cccttcct 28

<210> SEQ ID NO 164
<211> LENGTH: 28
<212> TYPE: DNA
<213> ORGANISM: artificial sequence
<220> FEATURE:
<223> OTHER INFORMATION: Synthetic

<400> SEQUENCE: 164
cagtcatttg gcgcccctgg gcctatcc 28

<210> SEQ ID NO 165
<211> LENGTH: 28
<212> TYPE: DNA
<213> ORGANISM: artificial sequence
<220> FEATURE:
<223> OTHER INFORMATION: Synthetic

<400> SEQUENCE: 165
cagtcatttg gctcaagagc aataacga 28

<210> SEQ ID NO 166
<211> LENGTH: 28
<212> TYPE: DNA
<213> ORGANISM: artificial sequence
<220> FEATURE:
<223> OTHER INFORMATION: Synthetic

<400> SEQUENCE: 166
cagtcatttg gccacgctca tgcacaca 28

<210> SEQ ID NO 167
<211> LENGTH: 28
<212> TYPE: DNA
<213> ORGANISM: artificial sequence
<220> FEATURE:
<223> OTHER INFORMATION: Synthetic

<400> SEQUENCE: 167
cagtcatttg gctgcggggc tagggcta 28

<210> SEQ ID NO 168
<211> LENGTH: 28
<212> TYPE: DNA
<213> ORGANISM: artificial sequence
<220> FEATURE:
<223> OTHER INFORMATION: Synthetic

<400> SEQUENCE: 168
cagtcatttg gccacccgta gaaccgac 28

<210> SEQ ID NO 169
<211> LENGTH: 28
<212> TYPE: DNA
<213> ORGANISM: artificial sequence
<220> FEATURE:
<223> OTHER INFORMATION: Synthetic

<400> SEQUENCE: 169
cagtcatttg gctcacaatg ctgacact 28

<210> SEQ ID NO 170
<211> LENGTH: 28
<212> TYPE: DNA
<213> ORGANISM: artificial sequence
<220> FEATURE:
<223> OTHER INFORMATION: Synthetic

<400> SEQUENCE: 170
cagtcatttg gctctccggg gaggcagg 28

<210> SEQ ID NO 171
<211> LENGTH: 24
<212> TYPE: DNA
<213> ORGANISM: artificial sequence
<220> FEATURE:
<223> OTHER INFORMATION: Synthetic

<400> SEQUENCE: 171
gcctcccact gcttcacttg acta 24

<210> SEQ ID NO 172
<211> LENGTH: 23
<212> TYPE: DNA
<213> ORGANISM: artificial sequence
<220> FEATURE:
<223> OTHER INFORMATION: Synthetic

<400> SEQUENCE: 172
ccgttttttt tttttaacca cac 23

<210> SEQ ID NO 173
<211> LENGTH: 23
<212> TYPE: DNA
<213> ORGANISM: artificial sequence
<220> FEATURE:
<223> OTHER INFORMATION: Synthetic

<400> SEQUENCE: 173
ccgttttttt tttttaacta tac 23

<210> SEQ ID NO 174
<211> LENGTH: 23
<212> TYPE: DNA
<213> ORGANISM: artificial sequence
<220> FEATURE:
<223> OTHER INFORMATION: Synthetic

<400> SEQUENCE: 174
ccgttttttt tttttcacag gtt 23

<210> SEQ ID NO 175
<211> LENGTH: 23
<212> TYPE: DNA
<213> ORGANISM: artificial sequence
<220> FEATURE:
<223> OTHER INFORMATION: Synthetic

<400> SEQUENCE: 175
ccgttttttt tttttcgcat tat 23

<210> SEQ ID NO 176
<211> LENGTH: 23
<212> TYPE: DNA
<213> ORGANISM: artificial sequence
<220> FEATURE:
<223> OTHER INFORMATION: Synthetic

<400> SEQUENCE: 176
ccgttttttt tttttccgtg gtt 23

<210> SEQ ID NO 177
<211> LENGTH: 23
<212> TYPE: DNA
<213> ORGANISM: artificial sequence
<220> FEATURE:
<223> OTHER INFORMATION: Synthetic

<400> SEQUENCE: 177
ccgttttttt tttttccata aag 23

<210> SEQ ID NO 178
<211> LENGTH: 23
<212> TYPE: DNA
<213> ORGANISM: artificial sequence
<220> FEATURE:
<223> OTHER INFORMATION: Synthetic

<400> SEQUENCE: 178
ccgttttttt tttttactag act 23

<210> SEQ ID NO 179
<211> LENGTH: 22
<212> TYPE: DNA
<213> ORGANISM: artificial sequence
<220> FEATURE:
<223> OTHER INFORMATION: Synthetic

<400> SEQUENCE: 179
cgtttttttt ttttcagctg ct 22

<210> SEQ ID NO 180
<211> LENGTH: 23
<212> TYPE: DNA
<213> ORGANISM: artificial sequence
<220> FEATURE:
<223> OTHER INFORMATION: Synthetic

<400> SEQUENCE: 180
ccgttttttt tttttggggt att 23

<210> SEQ ID NO 181
<211> LENGTH: 23
<212> TYPE: DNA
<213> ORGANISM: artificial sequence
<220> FEATURE:
<223> OTHER INFORMATION: Synthetic

<400> SEQUENCE: 181
ccgttttttt tttttggaaa tcc 23

<210> SEQ ID NO 182
<211> LENGTH: 23
<212> TYPE: DNA
<213> ORGANISM: artificial sequence
<220> FEATURE:
<223> OTHER INFORMATION: Synthetic

<400> SEQUENCE: 182
ccgttttttt tttttctgtt cct 23

<210> SEQ ID NO 183
<211> LENGTH: 23
<212> TYPE: DNA
<213> ORGANISM: artificial sequence
<220> FEATURE:
<223> OTHER INFORMATION: Synthetic

<400> SEQUENCE: 183
ccgttttttt tttttgcgga act 23

<210> SEQ ID NO 184
<211> LENGTH: 23
<212> TYPE: DNA
<213> ORGANISM: artificial sequence
<220> FEATURE:
<223> OTHER INFORMATION: Synthetic

<400> SEQUENCE: 184
ccgttttttt tttttctcaa tag 23

<210> SEQ ID NO 185

<211> LENGTH: 23
<212> TYPE: DNA
<213> ORGANISM: artificial sequence
<220> FEATURE:
<223> OTHER INFORMATION: Synthetic

<400> SEQUENCE: 185
ccgttttttt tttttaaccg att 23

<210> SEQ ID NO 186
<211> LENGTH: 23
<212> TYPE: DNA
<213> ORGANISM: artificial sequence
<220> FEATURE:
<223> OTHER INFORMATION: Synthetic

<400> SEQUENCE: 186
ccgttttttt tttttcttcc agt 23

<210> SEQ ID NO 187
<211> LENGTH: 23
<212> TYPE: DNA
<213> ORGANISM: artificial sequence
<220> FEATURE:
<223> OTHER INFORMATION: Synthetic

<400> SEQUENCE: 187
ccgttttttt tttttgctgt aaa 23

<210> SEQ ID NO 188
<211> LENGTH: 23
<212> TYPE: DNA
<213> ORGANISM: artificial sequence
<220> FEATURE:
<223> OTHER INFORMATION: Synthetic

<400> SEQUENCE: 188
ccgttttttt tttttactgg agg 23

<210> SEQ ID NO 189
<211> LENGTH: 23
<212> TYPE: DNA
<213> ORGANISM: artificial sequence
<220> FEATURE:
<223> OTHER INFORMATION: Synthetic

<400> SEQUENCE: 189
ccgttttttt tttttctagg ata 23

<210> SEQ ID NO 190
<211> LENGTH: 23
<212> TYPE: DNA
<213> ORGANISM: artificial sequence
<220> FEATURE:
<223> OTHER INFORMATION: Synthetic

<400> SEQUENCE: 190
ccgttttttt tttttacatt ttt 23

<210> SEQ ID NO 191
<211> LENGTH: 23
<212> TYPE: DNA
<213> ORGANISM: artificial sequence
<220> FEATURE:
<223> OTHER INFORMATION: Synthetic

<400> SEQUENCE: 191

```
ccgttttttt tttttgtggg tgt                                              23


<210> SEQ ID NO 192
<211> LENGTH: 23
<212> TYPE: DNA
<213> ORGANISM: artificial sequence
<220> FEATURE:
<223> OTHER INFORMATION: Synthetic

<400> SEQUENCE: 192

ccgttttttt tttttgctgt tag                                              23


<210> SEQ ID NO 193
<211> LENGTH: 23
<212> TYPE: DNA
<213> ORGANISM: artificial sequence
<220> FEATURE:
<223> OTHER INFORMATION: Synthetic

<400> SEQUENCE: 193

ccgttttttt tttttcgcaa ggt                                              23


<210> SEQ ID NO 194
<211> LENGTH: 23
<212> TYPE: DNA
<213> ORGANISM: artificial sequence
<220> FEATURE:
<223> OTHER INFORMATION: Synthetic

<400> SEQUENCE: 194

ccgttttttt tttttgtcag cag                                              23


<210> SEQ ID NO 195
<211> LENGTH: 23
<212> TYPE: DNA
<213> ORGANISM: artificial sequence
<220> FEATURE:
<223> OTHER INFORMATION: Synthetic

<400> SEQUENCE: 195

ccgttttttt tttttcacat tcc                                              23


<210> SEQ ID NO 196
<211> LENGTH: 18
<212> TYPE: DNA
<213> ORGANISM: artificial sequence
<220> FEATURE:
<223> OTHER INFORMATION: Synthetic

<400> SEQUENCE: 196

aaaaccgata gtgagtcg                                                    18
```

METHODS AND COMPOSITIONS FOR DETERMINING HEART FAILURE OR A RISK OF HEART FAILURE

CROSS REFERENCE TO RELATED APPLICATIONS

This application is a National Phase Application of PCT International Application PCT/IL2012/000201, filed May 23, 2012, which claims priority, under 35 U.S.C. §119(e), to and the benefit of U.S. Provisional Application No. 61/489,272, filed May 24, 2011, both of which are incorporated by reference herein in their entirety.

FIELD OF THE INVENTION

The invention relates in general to microRNA molecules associated with heart failure, as well as various nucleic acid molecules relating thereto or derived thereof.

BACKGROUND OF THE INVENTION

Heart failure is a pathophysiological state in which the heart is unable to pump sufficient blood to meet the nutrition and oxygen requirement of metabolizing tissues or cells. It is a major complication in many heart diseases. Adults over the age of 40 have an estimated 21% lifetime risk of developing heart failure (Lloyd-Jones et al., 2002, Circulation 106, 3068-72), a condition responsible for more hospitalizations than all forms of cancer combined (American Heart Association. Heart Disease and Stroke Statistics 2003 Update).

Research performed over the last several years demonstrated that transcriptional control and cardiac gene expression seems to play an important role in the pathogenesis and clinical manifestations of heart failure (HF) (Li et al., 2011, Cardiovasc Res. (6):498-512).

Specifically, previous studies demonstrated down-regulation of messenger RNA (mRNA) in HF patients suggesting the importance of molecular mechanisms that suppress mRNA steady state levels (Kaab et al., 2004, J Mol. Med. 82: 308-316).

In recent years, microRNAs (miRNAs, miRs) have emerged as an important novel class of regulatory RNA, which have a profound impact on a wide array of biological processes.

These small (typically 17-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. There are currently about 1223 known human miRs.

Recent data indicates that miRs are also associated with cardiac disease, HF included, and were even more sensitive than mRNAs to the acute functional status of end-stage heart failure (Thum et al., 2007, Circulation. 116: 258-267; Matkovich et al., 2009, Circulation. 119(9):1263-1271).

Current treatments for heart failure include pharmacological methods, devices such as the ventricular assist device (VAD), cardiac resynchronization therapy (CRT), implantable cardioverter-defibrillator (ICD) which is a small battery-powered and heart transplantation. Pharmacological approaches include but are not limited to the use of inotropic agents (i.e., compounds that increase cardiac contractility), neurohumoral blockers (e.g., beta-blockers, angiotensin converting enzyme inhibitors), aldosterone antagonists, diuretics, and vasodilators. However, none of these agents is fully effective either alone or in combination. Availability of transplants is highly limited, and since many individuals suffering from heart failure are in poor health, they are frequently not good surgical candidates. For these reasons, heart failure remains a major cause of morbidity and mortality, particularly in the developed world. In addition, it can be difficult to determine the precise etiology of heart failure, a factor impeding the development of more specific therapies. There is a general lack of diagnostic techniques at the molecular level. Thus, there is a need in the art for the discovery of circulating diagnostic markers which more accurately reflect the genetic predisposition of a subject of developing HF.

SUMMARY OF THE INVENTION

The present invention is based in part on the discovery of a panel of miRs whose levels are increased or decreased in the circulation of chronic systolic HF patients. Accordingly, an extensive panel of miRs was screened in the sera of stable chronic systolic HF patients and the results were compared to an age, gender and ethnically matched control group. A score based on the levels of miRs detected in serum was found which is suggestive of HF patients and is correlated with other known prognostic clinical markers in the HF group Circulating nucleic acids in body fluids offer unique opportunities for early diagnosis of the risk of HF. The present invention provides specific nucleic acid sequences for use in the identification, early detection and diagnosis of HF. The nucleic acid sequences can also be used as prognostic markers for prognostic evaluation of a subject based on their expression pattern in a biological sample. The invention further provides a method of minimally-invasive early detection or predisposition of HF.

The invention further provides a method of diagnosing or prognosticating heart failure in a subject, the method comprising: obtaining a biological sample from a subject; determining an expression profile in said sample of a nucleic acid sequence selected from the group consisting of SEQ ID NOS: 1-48, 94-146; a fragment thereof or a sequence having at least about 80% identity thereto; and comparing said expression profile to a reference expression profile wherein a difference in the level of expression profile in at least one or more nucleic acid sequence in said biological sample compared to said reference expression profile is diagnostic or prognostic for heart failure.

According to some embodiments, relatively high expression levels of a nucleic acid sequence selected from the group consisting of SEQ ID NOS: 1-39, 94-97, 119-122; a fragment thereof and a sequence having at least about 80% identity thereto is diagnostic or prognostic for heart failure.

According to other embodiments, relatively low expression levels of a nucleic acid sequence selected from the group consisting of SEQ ID NOS: 40-48, 98-118, 123-146; a fragment thereof and a sequence having at least about 80% identity thereto is diagnostic or prognostic for heart failure.

According to some embodiments, said method further comprising managing subject treatment based on the heart disease status.

According to some embodiments, said biological sample is selected from the group consisting of bodily fluid, a cell line and a tissue sample. According to one embodiment, the bodily fluid sample is a serum sample. According to another embodiment, said bodily fluid sample is a blood sample.

According to some embodiments, the method comprises determining the expression of at least two nucleic acid sequences. According to some embodiments the method further comprising combining one or more expression ratios. According to some embodiments, the expression levels are determined by a method selected from the group consisting of nucleic acid hybridization, nucleic acid amplification, and a combination thereof. According to some embodiments, the nucleic acid amplification method is real-time PCR(RT-PCR). According to one embodiment, said real-time PCR is quantitative real-time PCR (qRT-PCR).

According to some embodiments, the RT-PCR method comprises forward and reverse primers. According to other embodiments, the forward primer comprises a sequence selected from the group consisting of SEQ ID NOS: 49-66, 86-89, 147-171; a fragment thereof and a sequence having at least about 80% identity thereto. According to some embodiments, the real-time PCR method further comprises hybridization with a probe.

According to some embodiments, the probe comprises a nucleic acid sequence that is complementary to a sequence selected from the group consisting of any one of SEQ ID NOS: 1-48, 94-146; a fragment thereof and sequences at least about 80% identical thereto.

According to other embodiments, the probe comprises a sequence selected from the group consisting of any one of SEQ ID NOS: 67-84, 90-93, 172-196; a fragment thereof and a sequence having at least about 80% identity thereto.

The invention further provides a kit for assessing heart disease in a subject; said kit comprises a probe comprising a nucleic acid sequence that is complementary to a sequence selected from the group consisting of any one of SEQ ID NOS: 1-48, 94-146; a fragment thereof and sequences having at least about 80% identity thereto. According to some embodiments, said probe comprising a nucleic acid sequence selected from the group consisting of SEQ ID NOS: 67-84, 90-93, 172-196; a fragment thereof and sequences having at least about 80% identity thereto. According to other embodiments, the kit further comprises a forward primer comprising a sequence selected from the group consisting of SEQ ID NOS: 49-66, 86-89, 147-171; a fragment thereof and sequences having at least about 80% identity thereto. According to other embodiments, the kit further comprises a reverse primer comprising SEQ ID NO: 85, a fragment thereof and sequences having at least about 80% identity thereto.

These and other embodiments of the present invention will become apparent in conjunction with the figures, description and claims that follow.

Boxplots show the median (horizontal line), 25 to 75 percentile (box), extent of data up to 1.5 times the interquartile range ("whiskers"), and outliers (crosses).

FIGS. 2A-2D are boxplots presentations comparing distributions of the expression (Y axis) of exemplified down-regulated statistically significant microRNAs: hsa-miR-26a (SEQ ID NO: 40) (2A), hsa-miR-199b-5p (SEQ ID NO: 42) (2B), hsa-miR-33a (SEQ ID NO: 41) (2C) and hsa-miR-27b (SEQ ID NO: 43) (2D), in serum samples obtained from HF group (I) or healthy subjects (II). The results are based on Real time PCR, and a higher normalized signal indicates higher amounts of microRNA present in the samples.

Boxplots show the median (horizontal line), 25 to 75 percentile (box), extent of data up to 1.5 times the interquartile range ("whiskers"), and outliers (crosses).

Figure 1A:
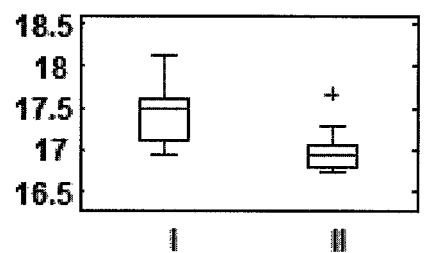
FIGS. 1A-1D are boxplots presentations comparing distributions of the presence of exemplified upregulated statistically significant microRNAs: hsa-miR-423-5p (SEQ ID NO: 13) (1A), hsa-miR-320a (SEQ ID NO: 1) (1B), hsa-miR-22 (SEQ ID NO: 14) (1C) and hsa-miR-92b (SEQ ID NO: 15) (1D), in serum samples obtained from HF group (I) or healthy subjects (II). The results are based on Real time PCR, and a higher normalized signal indicates higher amounts of microRNA present in the samples.
Figure 1B:
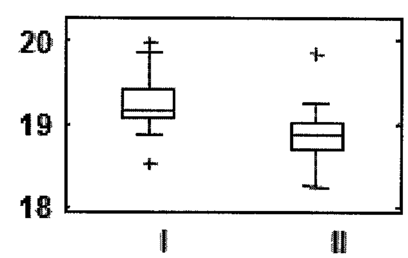
Figure 1C:
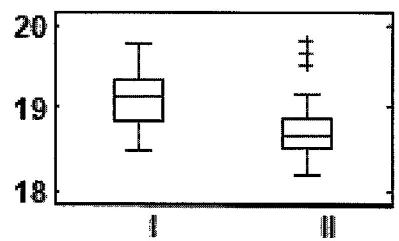
Figure 1D:
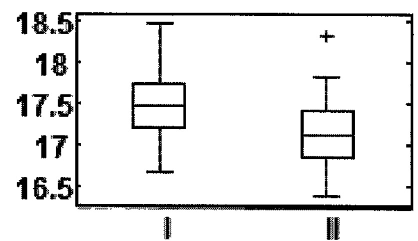
Figure 2A:
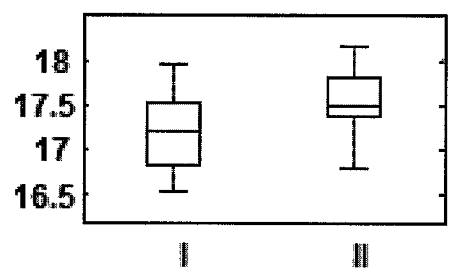
Figure 2B:
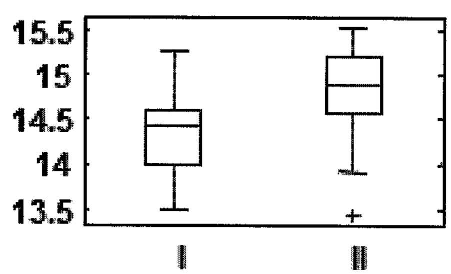
Figure 2C:
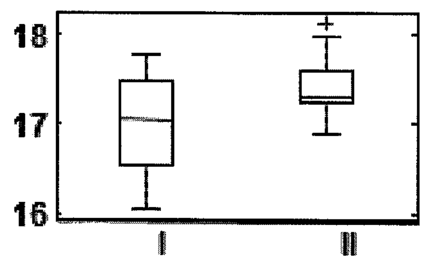
Figure 2D:
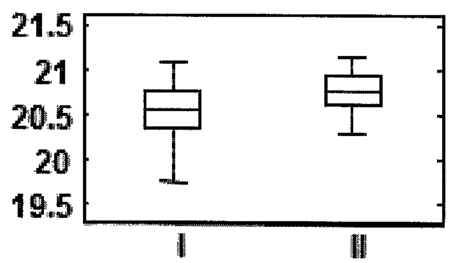
Figure 3:
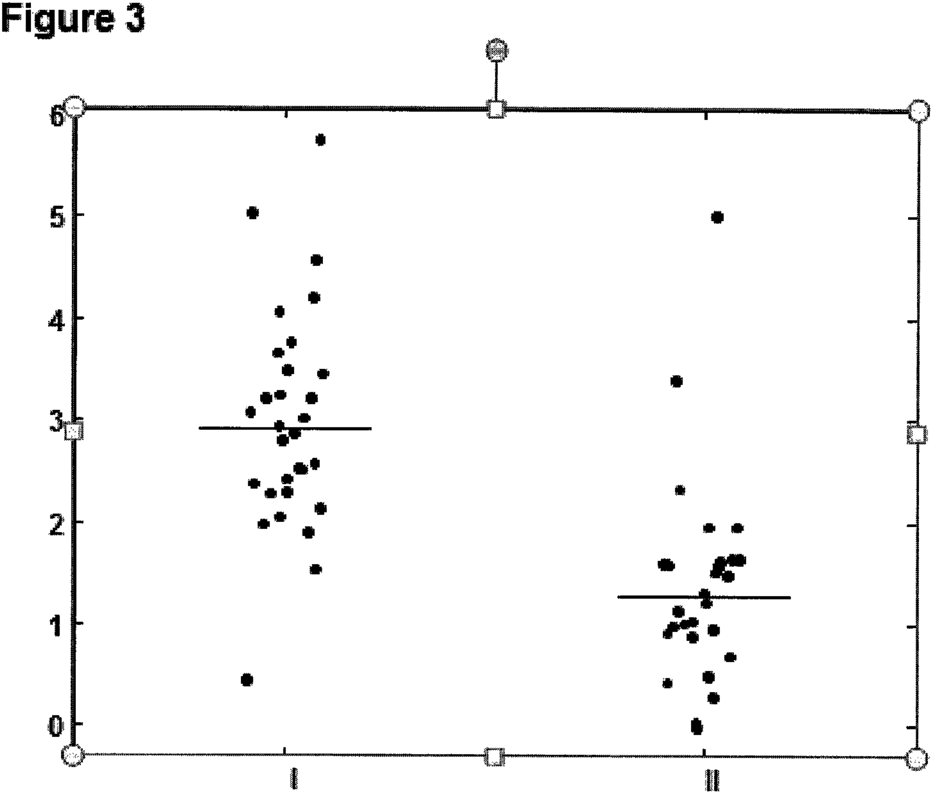

FIG. 3 is a dot plot showing that the miR-score (Y axis) significantly separates between the HF group (I) and the Control group (II). The miR-score was calculated for each sample as the mean normalized-inverted signal of hsa-miR-423-5p (SEQ ID NO: 13), hsa-miR-320a (SEQ ID NO: 1), hsa-miR-22 (SEQ ID NO: 14) and hsa-miR-92b (SEQ ID NO: 15) and adjusted by subtracting a constant (the minimal score) so that the range of scores starts at 0.

The horizontal lines indicate median values which are 2.9 in the HF group and 1.3 in the Control group. P-value for the two-sided unpaired t-test is 0.0000001

Figure 4:
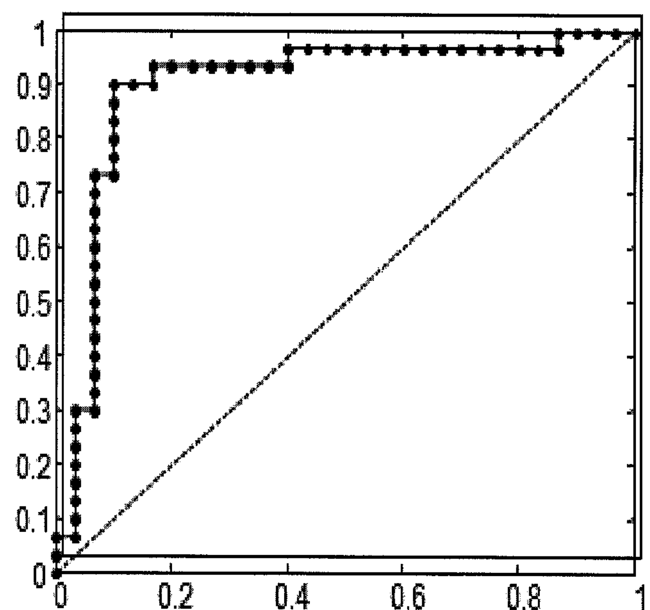

FIG. 4 is a Receiver Operating Characteristic (ROC) curve for miR-score discrimination between HF and Control groups. The ROC curve plots the sensitivity (Y axis) against the false-positive rate (one minus the specificity) (X axis) for different cutoff values of a diagnostic metric, and is a measure of classification performance. The area under the ROC curve (AUC) can be used to assess the diagnostic performance of the metric. A random classifier has AUC=0.5, and an optimal classifier with perfect sensitivity and specificity of 100% has AUC=1. The corresponding ROC curve has AUC=0.90.

Figure 5:
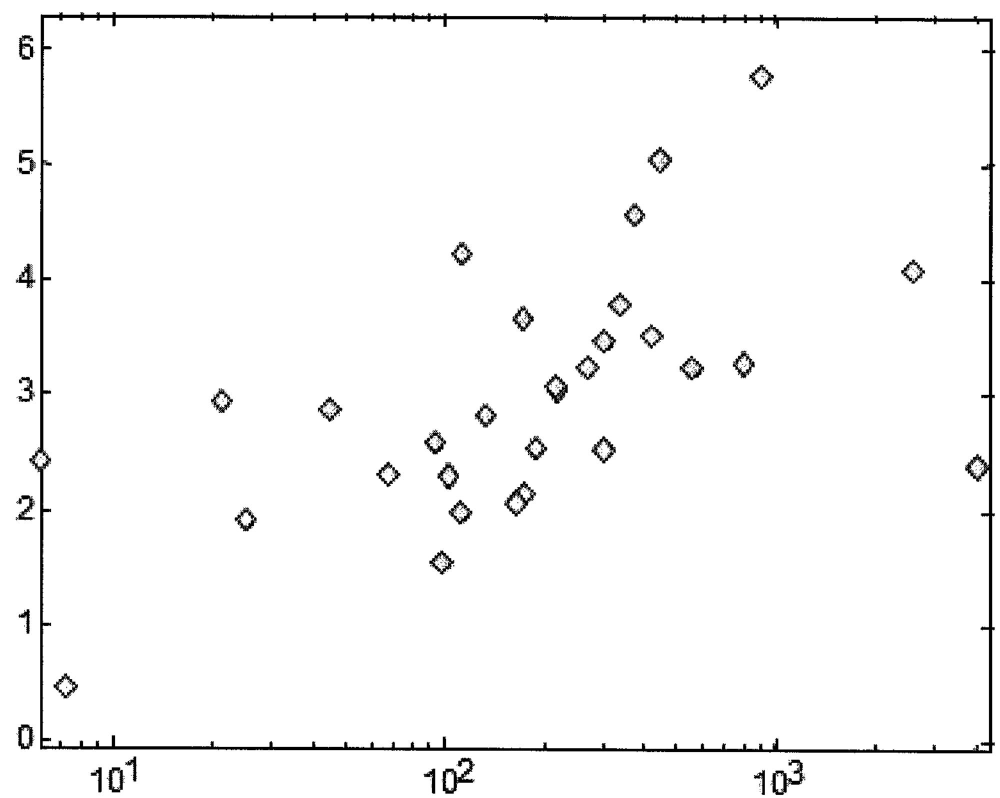

FIG. 5 is a plot demonstrating the significant correlation between miR-scores within the HF group (Y axis) and elevated serum Brain natriuretic peptide (BNP) levels (X axis). BNP levels for patients in the HF group are displayed in logarithmic scale. Spearman correlation of the BNP levels to the miRNA-score is 0.63 (p=0.003).

Figure 6:
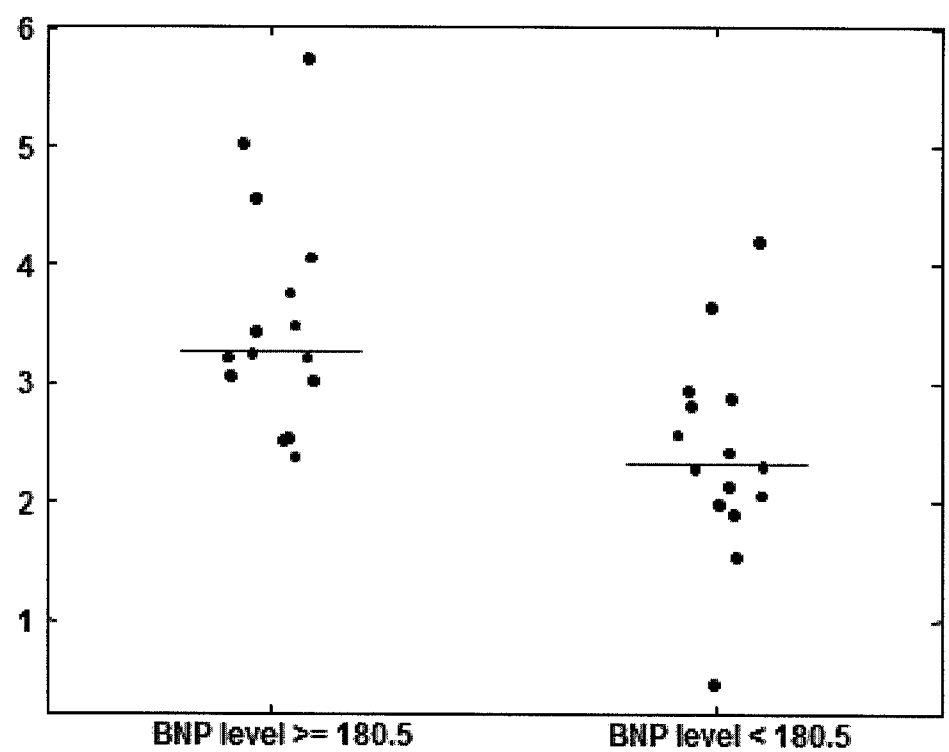

FIG. 6 is a dot plot demonstrating the significant association between miR-scores (Y axis) and serum Brain natriuretic peptide (BNP) levels (X axis). The miR-scores were compared between samples from HF patients whose values for the parameter were in the upper half to the samples whose values were in the lower half. High BNP levels are associated with high miRNA-score, p value=0.002.

Figure 7:
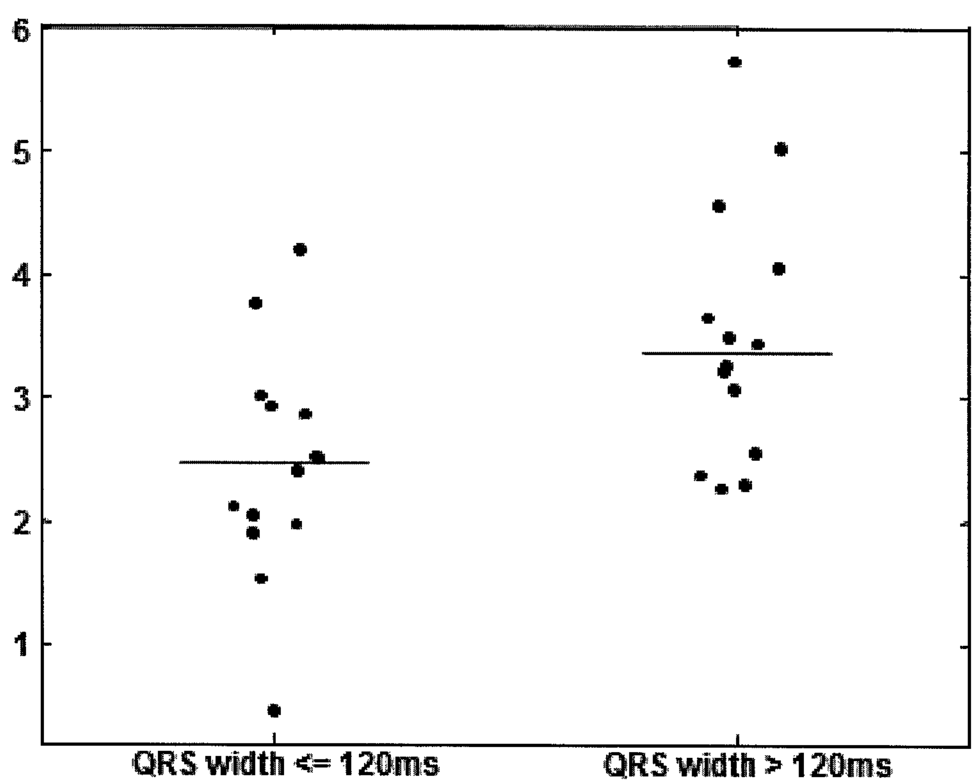

FIG. 7 is a dot plot demonstrating the significant association between miR-scores (Y axis) and wide QRS (X axis). p value=0.009.

Figure 8:
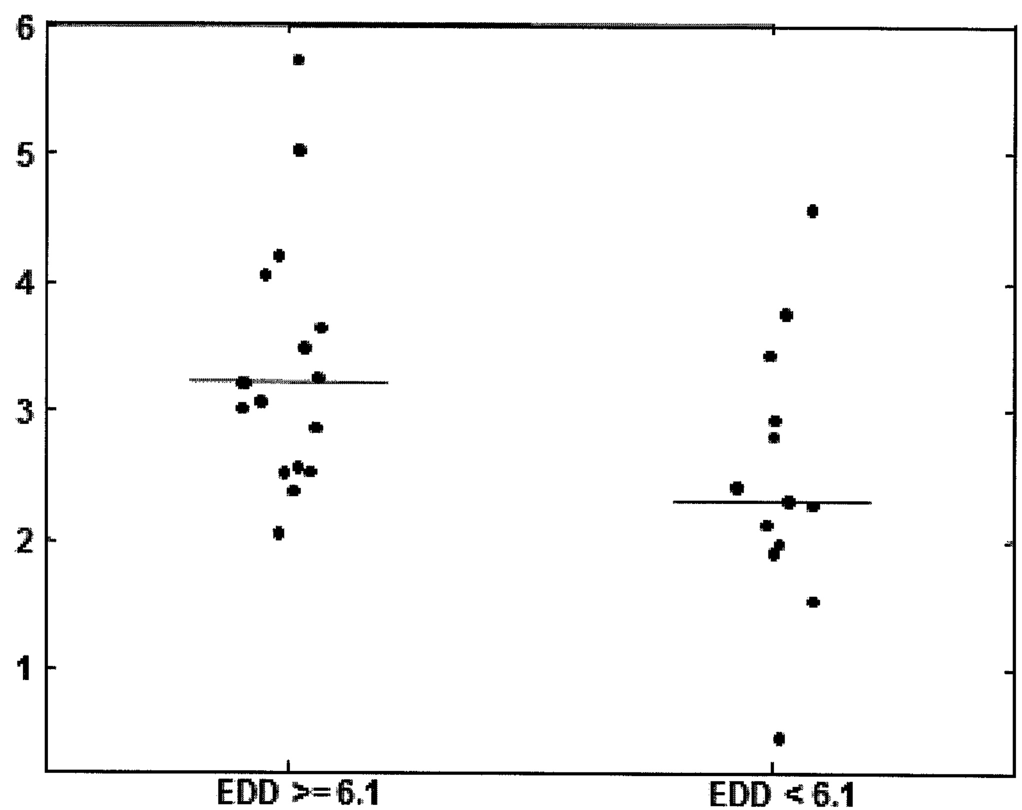

FIG. 8 is a dot plot demonstrating the significant association between miR-scores (Y axis) and Left ventricular end diastolic dimension (EDD) (X axis). High end diastolic diameter (EDD) is associated with high miRNA score (p=0.03).

Figure 9:
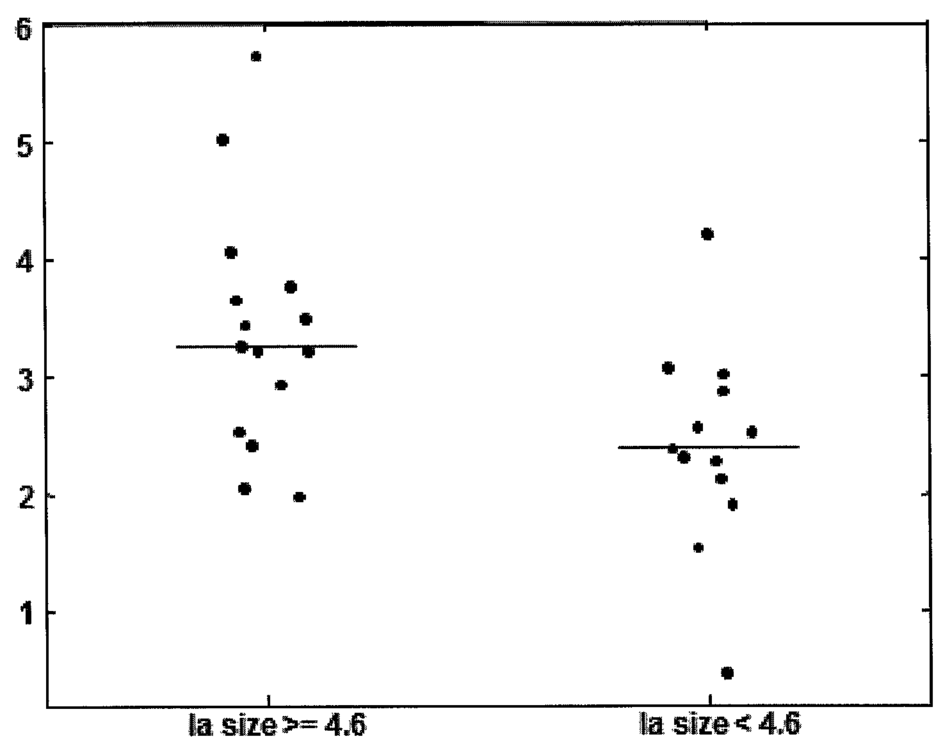

FIG. 9 is a dot plot demonstrating the significant association between miR-scores (Y axis) and Left atrial dimension (LAD) (X axis). High LAD is associated with high miRNA score (p=0.01).

DETAILED DESCRIPTION OF THE INVENTION

The invention is based in part on the discovery that specific biomarker sequences (SEQ ID NOS: 1-48, 94-146)

can be used for the identification, early detection, diagnosis and prognosis of heart failure.

Biomarkers have the potential to revolutionize diagnosis and treatment of various medical conditions. Ideally, biomarkers should be sampled in a minimal-invasive way. Therefore the challenge of diverse biomedical research fields has been to identify biomarkers in body fluids, such as serum or blood. In recent years it has become clear that both cell-free DNA and mRNA are present in serum, as well as in other body fluids, and represent potential biomarkers. However, monitoring the typically small amounts of these nucleic acids in body fluids requires sensitive detection methods, which are not currently clinically applicable.

The present invention provides a sensitive, specific and accurate method which can be used for conducting in a minimally-invasive early detection, diagnosis and prognosis of heart failure. The methods of the present invention have high sensitivity and specificity.

Surprisingly, the above method allows simple minimally-invasive test, for easy detection of heart disease at a very early stage with higher reliability and effectiveness, saving time, material and operating steps, as well as saving cost and fine chemicals difficult to obtain.

Furthermore, the method according to the invention combines the advantages of easy sample collection and the option of diagnosing heart failure at an early stage. Being a minimally-invasive method, in which e.g. delivering a sample of serum, the method has a good potential to achieve high acceptance among subjects, which subjects can be humans or animals, for example. Therefore, the method can be used in routine tests, but also in prophylactic medical examinations.

Also, the present invention provides methods for determining a treatment plan. Once the health care provider knows to which disease class the sample, and therefore, the individual belongs, the health care provider can determine an adequate treatment plan for the individual. For example, different heart disease classes often require differing treatments. As described herein, individuals having a particular type or class of heart disease can benefit from a different course of treatment, than an individual having a different type or class of heart disease. Properly diagnosing and understanding the class of heart disease of an individual allows for a better, more successful treatment and prognosis.

Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

About

As used herein, the term "about" refers to +/−10%.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein refer to a probe and a solid support and may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe, or both. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Classification

"Classification" as used herein refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to one embodiment, classification means determination of the type of heart disease.

Complement

"Complement" or "complementary" as used herein means Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

$C_T$ $C_T$ signals represent the first cycle of PCR where amplification crosses a threshold (cycle threshold) of fluorescence. Accordingly, low values of $C_T$ represent high abundance or expression levels of the microRNA.

In some embodiments the PCR $C_T$ signal is normalized such that the normalized $C_T$ remains inversed from the expression level. In other embodiments the PCR $C_T$ signal may be normalized and then inverted such that low normalized-inverted $C_T$ represents low abundance or expression levels of the microRNA.

Detection

"Detection" means detecting the presence of a component in a sample. Detection also means detecting the absence of a component. Detection also means measuring the level of a component, either quantitatively or qualitatively.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cDNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. According to some embodiments, the term "expression profile" means measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Heart Disease

As used herein heart disease relates to the following non-limiting examples: Heart failure (congestive); Cardiomyopathies, such as Ischemic cardiomyopathy, Dilated cardiomyopathy, Hypertrophic cardiomyopathy, Restrictive cardiomyopathy, Alcoholic cardiomyopathy, Viral cardiomyopathy, Tachycardia-mediated cardiomyopathy, Stress-induced (takotsubo) cardiomyopathy, Amyloid cardiomyopathy, Arrhythmogenic right ventricular dysplasia, or unclassified cardiomyopathies, for example Left ventricular noncompaction or Endocardial fibroelastosis; or valvular heart disease, such as Aortic stenosis, Aortic regurgitation, Mitral stenosis, Mitral regurgitation, Mitral prolapse, Pulmonary stenosis, Pulmonary regurgitation, Tricuspid stenosis, or Tricuspid regurgitation.

Heart Failure

As used herein, the term "heart failure" broadly refers to any condition that reduces the ability of the heart to pump blood or pumping blood with elevated filling pressures. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease.

According to some embodiments, said heart failure refers to heart failure with preserved systolic function (HFPSF).

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

Label

"Label" as used herein means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Nucleic Acid

"Nucleic acid" or "oligonucleotide" or "polynucleotide" as used herein mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005) and Soutschek et al., Nature 432:173-178 (2004), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Reference Expression Profile

As used herein, the phrase "reference expression profile" refers to a criterion expression value to which measured values are compared in order to determine the detection of a subject with an heart disease. The reference may be based on a combine metric score.

Sensitivity

"sensitivity" used herein may mean a statistical measure of how well a binary classification test correctly identifies a condition, for example how frequently it correctly classifies an heart disease into the correct type. The sensitivity for class A is the proportion of cases that are determined to belong to class "A" by the test out of the cases that are in class "A", as determined by some absolute or gold standard.

Specificity

"Specificity" used herein may mean a statistical measure of how well a binary classification test correctly identifies a condition, for example how frequently it correctly classifies an heart disease into the correct type. The specificity for class A is the proportion of cases that are determined to belong to class "not A" by the test out of the cases that are in class "not A", as determined by some absolute or gold standard.

Standard Sample

A "standard sample" refers to a sample that is representative of a disease-free state, particularly a state in which heart failure or any other associated condition is absent (i.e. a healthy state). By way of example, the standard sample may be a biological sample, obtained from a healthy subject of similar age as the subject for whom the diagnosis or prognosis is provided. A standard sample may be a composite sample, wherein data obtained from biological samples from several healthy subjects (i.e. control subjects who do not have symptoms of heart failure) are averaged, thereby creating the composite sample.

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium).

Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Tissue Sample

As used herein, a tissue sample is tissue obtained from a tissue biopsy using methods well known to those of ordinary skill in the related medical arts. Methods for obtaining the sample from the biopsy include gross apportioning of a mass, microdissection, laser-based microdissection, or other art-known cell-separation methods.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNA for the identification, classification and diagnosis of heart disease.

MicroRNA Processing

A gene coding for a microRNA (miRNA) may be transcribed leading to production of an miRNA precursor known as the pri-miRNA. The pri-miRNA may be part of a polycistronic RNA comprising multiple pri-miRNAs. The pri-miRNA may form a hairpin structure with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nucleotide precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repression or activation), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have studied the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in miRNA binding. Moreover, sufficient base pairing at the 3' can compensate for insufficient pairing at the 5' (Brennecke et al, 2005 PLoS 3-e85).

Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acids comprise the sequence of SEQ ID NOS: 1-196 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single-or double-stranded form or capable of being expressed by a synthetic gene using methods well known to those skilled in the art, including as described in U.S. Pat. No. 6,506,559 which is incorporated by reference.

TABLE 1

The nucleic acid sequences of the present invention

| Hairpin SEQ ID | miR SEQ ID NO: | miR name |
|---|---|---|
| 32 | 13 | hsa-miR-423-5p |
| 19 | 1 | hsa-miR-320a |
| 33 | 14 | hsa-miR-22 |
| 34 | 15 | hsa-miR-92b |
| 20 | 2 | hsa-miR-17* |
| 21 | 3 | hsa-miR-532-3p |
| 35, 36 | 16 | hsa-miR-92a |
| 22 | 4 | hsa-miR-30a |
| 23 | 5 | hsa-miR-21 |
| 24, 25 | 6 | hsa-miR-101 |
| 26 | 7 | hsa-miR-363 |
| 27 | 8 | hsa-miR-346 |
| 28 | 9 | hsa-miR-20b |
| 29 | 10 | hsa-miR-25 |
| 37 | 17 | hsa-miR-486-3p |
| 30 | 11 | hsa-miR-185 |
| 31 | 12 | hsa-miR-451 |
| 38, 39 | 18 | hsa-miR-19b |
| 44, 45 | 40 | hsa-miR-26a |
| 46 | 41 | hsa-miR-33a |
| 47 | 42 | hsa-miR-199b-5p |
| 48 | 43 | hsa-miR-27b |
| 119 | 94 | hsa-miR-29c |
| 143 | 116 | MID-00630 |
| 120 | 95 | hsa-miR-30d |
| 121 | 96 | hsa-miR-140-3p |
| 122 | 97 | hsa-let-7b |
| 123 | 98 | hsa-miR-331-3p |
| 124 | 99 | hsa-miR-744 |
| 146 | 117 | MID-24705 |
| 125 | 100 | hsa-miR-28-5p |
| 126 | 101 | hsa-mIR-574-3p |
| 127 | 102 | hsa-miR-223 |
| 128 | 103 | hsa-miR-142-3p |
| 129 | 104 | hsa-miR-27a |
| 130 | 105 | hsa-mIR-191 |
| 131 | 106 | hsa-miR-335 |
| 132, 133 | 107 | hsa-mIR-24 |
| 134 | 108 | hsa-miR-151-5p |
| 135 | 109 | hsa-miR-126 |
| 144, 145 | 118 | MID-00108 |
| 136 | 110 | hsa-miR-125a-5p |
| 137, 138 | 111 | hsa-let-7f |
| 139 | 112 | hsa-miR-23a |
| 140 | 113 | hsa-miR-30e* |
| 141 | 114 | hsa-miR-326 |
| 142 | 115 | hsa-miR-99b |

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-48, 94-146; or variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm, with default parameters as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-48, 94-146; or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-18, 40-43, 94-115; or variants thereof.

Anti-miRNA

The nucleic acid may also comprise a sequence of an anti-miRNA capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-48, 94-146; or variants thereof.

Binding Site of Target

The nucleic acid may also comprise a sequence of a target microRNA binding site or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-18, 40-43, 94-115.

Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 67-84, 90-93, 172-196; or variants thereof.

Linker Sequences

The probe may further comprise a linker. The linker may be 10-60 nucleotides in length.

The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides. The forward primer may comprise SEQ ID NOS: 49-66, 86-89, 147-171; or variants thereof.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise SEQ ID NO: 85, or variants thereof.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined locations on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrate materials include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The substrate of the biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker.

The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostics

A method of diagnosis is also provided. The method comprises detecting a differential expression level of heart disease-associated nucleic acids in a biological sample. The sample may be derived from a patient. Diagnosis of heart disease state, and its histological type, in a patient may allow for prognosis and selection of therapeutic strategy.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

The following examples are presented in order to more fully illustrate some embodiments of the invention. They should, in no way be construed, however, as limiting the broad scope of the invention.

EXAMPLES

Example 1

Methods

Patient and Control's Cohort

Thirty patients with chronic stable, class C, systolic HF patients were recruited at the HF clinic in Lin Medical Center, Haifa Israel. In addition, another control group consistent of 30 volunteers who were age, gender and ethnically matched to the HF group were recruited. The study was approved by the Institution Review Board (Helsinki committee) of the Lady Davis Carmel Medical Center, and all patients gave written informed consent before inclusion in the study and the start of any study related procedures. The inclusion criteria for the HF group were: Chronic systolic HF patients, treated for at least 3 months according to the ACC/AHA guidelines, Stage C, clinically stable as judged by the treating HF specialized cardiology on day of recruitment. The inclusion criteria for the control group were: un-known or treated any coronary, valvular or myocardial disease. Comorbidities for coronary artery disease such as diabetes mellitus, hypertension, hyperlipidemia and smoking did not preclude recruitment. Exclusion criteria for all participants were: pregnancy, dialysis, known or treated malignancies. All the clinically relevant data was collected in the HF group: clinical, echocardiographic, electrocardiographic, baseline laboratory as well as the relevant demographic data in the Control group.

The characteristics of the HF group and the demographics of the HF and the Control groups are shown in Table 2.

TABLE 2

HF and control groups' characteristics

| P-value | Control group (n = 30) | HF group (n = 30) | Variable |
|---|---|---|---|
| 0.21 | 21 (70%) | 26 (87%) | Gender (male) |
| 0.57 | 63 ± 12.2 | 64.5 ± 9.3 | Age (years)* |
| 0.34 | 5 (17%) | 4 (13%) | Smoking |
| 0.09 | 27.5 ± 5.3 | 29.9 ± 5.6 | Body mass index |
| 0.003 | 2 (7%) | 17 (57%) | Diabetes Mellitus |
| 0.006 | 0 | 7 (23%) | Chronic Renal Failure (baseline creatinine > 1.5 mg/dl |
| <0.0001 | 9 (30%) | 28 (93%) | Angiotensin Receptor Blockers/ angiotensin-converting enzyme inhibitors |
| <0.0001 | 6 (20%) | 27 (90%) | Beta Blockers |
| 0.001 | 0 | 10 (33%) | Aldospirone |
| 0.03 | 16 (53%) | 24 (80%) | Statins |
| | N/A | 444.5 ± 835.0 | BNP (pg/ml)* |
| | N/A | 22 (73%) | Ischemic Etiology |
| | N/A | 2.4 ± 0.4 | NYHA Grade (1-4) |
| | N/A | 16 (53%) | Implantable cardio-verter defibrillator/ cardiac resynchro-nization therapy |
| 0.79 | Arabic 3 (10%) Ashkenazi 17 (56%) Sfaradi 8 (27%) Mixed Israeli Jewish 2 (7%) | Arabic 3 (10%) Ashkenazi 15 (50%) Sfaradi 10 (33%) Mixed Israeli Jewish 2 (7%) | Ethnicity |

*Means ± SD

As elaborated; the two groups (HF and Control) were similar in regarding to their age, gender, ethnicity, body mass index and smoking habits. Predicted and trivial significant changes, reflecting the different nature of the HF versus the Control group were in the medical regimens, anti-arrhythmic devices and the prevalence of comorbidities; including coronary artery disease, diabetes mellitus and chronic renal failure.

Serum Isolation and Storage 8 ml of blood was collected from each individual directly into serum collection tubes (Greiner Bio-one, VACUETTE® Serum Tubes 455071). The whole blood was allowed to stand for about 1 h at room temperature (RT) before being centrifuged at 1800 g for 10 minutes at RT. The resultant serum was aliquoted into eppendorf tubes and stored at −80° C.

Brain natriuretic peptide (BNP) levels were determined for simultaneous serum BNP levels (Triage MetrPro; BIO-SITE, San-Diego, Calif.).

RNA Extraction

Serum (100 μl) was incubated over night at 57° C. with 300 μl pre-heated Proteinase K extraction solution as detailed in Table 3:

TABLE 3

| Proteinase K extraction solution | | | |
|---|---|---|---|
| Final in 400 ul (serum + buffer) | Final | Stock | Component |
| 0.0885M | 0.118M | 5M | NaCl |
| 9 mM | 12 mM | 1M | Tris Hcl pH 8 |
| 32.25 mM | 47 mM | 1M | DTT |
| 9 mM | 12 mM | 0.5M | EDTA pH 8 |
| 1.8% (62.1 mM) | 2.4% (82.8 mM) | 20% (690 mM) | SDS |
| 2 mg/ml | 2.66 mg/ml | 20 mg/ml | Proteinase K ABI (20 mg/ml) |
| | | | DDW |

Followed by acid phenol:chloroform extraction, linear acrylamide (8 μl) was added. RNA was ETOH precipitated ON at −20° C. and re-suspend with DDW (43 μl). Next, DNase (Ambion) treatment was performed to eliminate residual DNA fragments. Finally, after a second acid phenol: chloroform extraction, the pellet was re-suspended in DDW.

Exosome Separation

Exosomal separation from serum was performed using the Exoquick kit (ExoQuick™ Exosome Precipitation Solution Cat. # EXOQ20A-1, SBI) according to the manufacture instructions.

qRT-PCR

RNA was subjected to a polyadenylation reaction as described previously (Shi, R. and Chiang, V. L. 2005, Biotechniques. 39(4):519-25). Briefly, RNA was incubated in the presence of poly (A) polymerase (PAP; NEB-M0276L), MnCl2, and ATP for 1 h at 37° C. Then, using an oligodT primer harboring a consensus sequence (complementary to the reverse primer) reverse transcription was performed on total RNA using SuperScript II RT (Invitrogen). Next, the cDNA was amplified by real time PCR; this reaction contained a microRNA-specific forward primer, a TaqMan probe complementary to the 3' of the specific microRNA sequence as well as to part of the polyA adaptor sequence, and a universal reverse primer complementary to the consensus 3' sequence of the oligodT tail.

The negative controls studied along the RNA samples, serve to detect potential contaminations and/or non-specific amplifications. The cycle number at which the fluorescence passes the threshold (Cycle Threshold—Ct) was measured for each miRNA in each sample.

Serum miRNA Analysis 370 miRNAs which were detected in previous experiments performed by the inventors of the present invention in heart tissue or serum of healthy individual were measured in 4 pools created from sera of 6 HF patients and 6 healthy individuals and in a negative control. 186 of these miRNAs were reliably detected in at least one of the pools, with a difference of at least 3 CTs compared to the negative control. These 186 miRNAs were measured in the sera of all 60 participants and 2 negative controls using RT-PCR. 7 miRs for which the median Ct in the serum samples was less than 3 Cts lower than median Ct in the negative controls were omitted from analysis and normalization Data Analysis and Statistics Each sample was normalized by subtracting the average Ct of all miRs of the sample from the Ct of each miR, and adding back a scaling constant (the average Ct over the entire sample set). Normalized signals were compared between groups of in order to find miRs which can be used to differentiate between the groups. Significance of differences was assessed by a two-sided unpaired t-test. The Benjamini-Hochberg False Discovery Rate (FDR) method (Benjamini et al., 1995, J. Roy. Statist. Soc. Ser. B 57 no. 1, 289-300) was used to control for multiple hypotheses testing, using an FDR of 0.1. Fold-change was calculated as absolute difference in median values of the normalized Ct in the two groups.

For each miRNA as well as for the miRNA score the ability to discriminate between HF and Control groups was characterized by the receiver operating characteristic (ROC) curve and the area under the ROC curve (AUC) was calculated.

For the box plots and the score calculation, inverted-normalized signals were used such that high values represent high expression. The inverted-normalized signal for each miR is calculated by subtracting the normalized CT from 50.

Leave-one-out cross validation with a logistic regression model was used to simulate the performance of a classification algorithm on unseen samples. The logistic regression model was repeatedly retrained, leaving out one sample in each round, and testing each sample on a classifier that was trained without it. Associations between the score and clinical/prognostic variables: For dichotomous variables a two-sided unpaired t-test was used to compare the scores of the patients in the two groups. For continuous variables a two-sided unpaired t-test was used to compare the score of samples whose values were in the upper half to the samples whose values were in the lower half. The correlation between BNP and the score was measured using the Spearman rank coefficient as the relation is not linear.

Chi-square tests were used to compare categorical variables. Fisher's Exact Test was used in cases of small sample sizes.

Example 2

Specific microRNAs are Used for the Detection of HF in Serum Samples

The levels of 186 microRNAs were measured in all of the serum samples and normalized as described in the methods section. The signals for the 30 samples in the Heart Failure group were compared to the signals of the 30 samples in the Control group. A total of 47 miRs passed the FDR threshold of 0.1 (p value cut off 0.027). Out of these, the median levels 18 miRs in the sera of the Heart Failure group were over 1.2 fold higher than those detected in sera of controls.

TABLE 4A

| Up-regulated miRs in Heart Failure group vs. Control group | | | | | |
|---|---|---|---|---|---|
| median values** | | AUC* | fold-change | p-value | miR name |
| 16.922 | 17.485 | 0.88 | 1.48 (+) | 1.80E−08 | hsa-miR-423-5p |
| 18.883 | 19.156 | 0.86 | 1.21 (+) | 1.50E−05 | hsa-miR-320a |
| 18.655 | 19.119 | 0.8 | 1.38 (+) | 1.30E−04 | hsa-miR-22 |
| 17.128 | 17.467 | 0.76 | 1.26 (+) | 4.50E−04 | hsa-miR-92b |
| 14.435 | 14.823 | 0.76 | 1.31 (+) | 7.50E−04 | hsa-miR-17* |
| 13.857 | 14.308 | 0.73 | 1.37 (+) | 8.20E−04 | hsa-miR-532-3p |
| 21.885 | 22.34 | 0.74 | 1.37 (+) | 1.90E−03 | hsa-miR-92a |
| 17.161 | 17.677 | 0.73 | 1.43 (+) | 2.90E−03 | hsa-miR-30a |
| 20.411 | 20.735 | 0.72 | 1.25 (+) | 4.20E−03 | hsa-miR-21 |
| 18.081 | 18.287 | 0.72 | 1.15 (+) | 5.20E−03 | hsa-miR-29c |
| 16.713 | 17.145 | 0.71 | 1.35 (+) | 7.20E−03 | hsa-miR-101 |
| 16.855 | 17.419 | 0.71 | 1.48 (+) | 7.80E−03 | hsa-miR-363 |

TABLE 4A-continued

| Up-regulated miRs in Heart Failure group vs. Control group | | | | | |
|---|---|---|---|---|---|
| median values** | | AUC* | fold-change | p-value | miR name |
| 13.739 | 13.988 | 0.68 | 1.19 (+) | 8.30E−03 | MID-00630 (0.6) |
| 12.415 | 12.866 | 0.69 | 1.37 (+) | 8.40E−03 | hsa-miR-346 (0.7) |
| 16.833 | 17.362 | 0.72 | 1.44 (+) | 8.50E−03 | hsa-miR-20b |
| 19.507 | 19.992 | 0.7 | 1.40 (+) | 1.20E−02 | hsa-miR-25 |
| 18.811 | 19 | 0.69 | 1.14 (+) | 1.30E−02 | hsa-miR-30d |
| 13.022 | 13.433 | 0.69 | 1.33 (+) | 1.30E−02 | hsa-miR-486-3p |
| 18.125 | 18.479 | 0.68 | 1.28 (+) | 1.50E−02 | hsa-miR-185 |
| 16.978 | 17.201 | 0.7 | 1.17 (+) | 1.60E−02 | hsa-miR-140-3p |
| 25.144 | 25.535 | 0.68 | 1.31 (+) | 1.60E−02 | hsa-miR-451 |
| 19.236 | 19.448 | 0.66 | 1.16 (+) | 2.10E−02 | hsa-let-7b |
| 21.402 | 21.769 | 0.66 | 1.29 (+) | 2.40E−02 | hsa-miR-19b |

TABLE 4B

| Down-regulated miRs in Heart Failure group vs. Control group | | | | | |
|---|---|---|---|---|---|
| median values** | | AUC* | fold-change | p-value | miR name |
| 17.501 | 17.211 | 0.76 | 1.22 (−) | 7.60E−05 | hsa-miR-26a |
| 14.884 | 14.427 | 0.79 | 1.37 (−) | 1.40E−04 | hsa-miR-199b-5p |
| 17.318 | 17.044 | 0.74 | 1.21 (−) | 3.80E−04 | hsa-miR-33a |

TABLE 4B-continued

| Down-regulated miRs in Heart Failure group vs. Control group | | | | | |
|---|---|---|---|---|---|
| median values** | | AUC* | fold-change | p-value | miR name |
| 20.785 | 20.574 | 0.72 | 1.16 (−) | 1.80E−03 | hsa-miR-27b |
| 15.374 | 15.024 | 0.73 | 1.27 (−) | 1.90E−03 | hsa-miR-331-3p |
| 14.694 | 14.341 | 0.71 | 1.28 (−) | 2.60E−03 | hsa-miR-744 |
| 21.356 | 21.023 | 0.72 | 1.26 (−) | 2.70E−03 | MID-24705 (0.7) |
| 17.272 | 16.979 | 0.7 | 1.23 (−) | 2.90E−03 | hsa-miR-28-5p |
| 14.59 | 14.221 | 0.73 | 1.29 (−) | 3.70E−03 | hsa-miR-574-3p |
| 22.219 | 21.984 | 0.7 | 1.18 (−) | 4.50E−03 | hsa-miR-223 |
| 19.917 | 19.618 | 0.7 | 1.23 (−) | 4.60E−03 | hsa-miR-142-3p |
| 21.656 | 21.448 | 0.7 | 1.15 (−) | 4.60E−03 | hsa-miR-27a |
| 16.922 | 16.752 | 0.69 | 1.13 (−) | 5.20E−03 | hsa-miR-191 |
| 14.8 | 14.478 | 0.71 | 1.25 (−) | 6.00E−03 | hsa-miR-335 |
| 19.551 | 19.32 | 0.7 | 1.17 (−) | 7.00E−03 | hsa-miR-24 |
| 16.297 | 15.872 | 0.68 | 1.34 (−) | 9.00E−03 | hsa-miR-151-5p |
| 20.092 | 19.82 | 0.68 | 1.21 (−) | 1.00E−02 | hsa-miR-126 |
| 11.868 | 10.733 | 0.66 | 2.20 (−) | 1.10E−02 | MID-00108 (0.7) |
| 15.497 | 15.359 | 0.66 | 1.10 (−) | 1.20E−02 | hsa-miR-125a-5p |
| 16.407 | 16.077 | 0.69 | 1.26 (−) | 1.50E−02 | hsa-let-7f |
| 22.104 | 21.918 | 0.68 | 1.14 (−) | 1.80E−02 | hsa-miR-23a |
| 14.255 | 13.995 | 0.7 | 1.20 (−) | 1.90E−02 | hsa-miR-30e* |
| 14.185 | 13.935 | 0.66 | 1.19 (−) | 2.00E−02 | hsa-miR-326 |
| 15.363 | 14.617 | 0.7 | 1.68 (−) | 2.20E−02 | hsa-miR-99b |

*AUC indicates the area under the ROC curve for the discrimination between HF and control groups.
**Median values are also given as normalized-inverted signals.

TABLE 5

| Sequences of primers and probes used for the detection of differential miRs | | | | |
|---|---|---|---|---|
| MGB SEQ ID NO: | MGB Sequence | FWD SEQ ID NO: | FWD | miR name |
| 67 | CCGTTTTTTTTTTTCGCCCTCT | 49 | CAGTCATTTGGGAAAAGCTGGGTTGAGA | hsa-miR-320a |
| 68 | CCGTTTTTTTTTTTCAGTTATC | 50 | CAGTCATTTGGCTACAGTACTGTGATAA | hsa-miR-101 |
| 69 | ATCCGTTTTTTTTTTTCTACAAGT | 51 | CAGTCATTTGGCACTGCAGTGAAGGCAC | hsa-miR-17* |
| 70 | CGTTTTTTTTTTTCAGGAACT | 52 | CAGTCATTTGGCTGGAGAGAAAGGCAGT | hsa-miR-185 |
| 71 | CGTTTTTTTTTTTCAGTTTTG | 53 | CAGTCATTTGGCTGTGCAAATCCATGCA | hsa-miR-19b |
| 72 | CCGTTTTTTTTTTTCTACCTGC | 54 | CAGTCATTTGGCCAAAGTGCTCATAGTG | hsa-miR-20b |
| 73 | CCGTTTTTTTTTTTCTTCCAGT | 55 | CAGTCATTTGGGTGTAAACATCCTCGAC | hsa-miR-30a |
| 74 | CCGTTTTTTTTTTTACAGATGG | 56 | CAGTCATTTGGCAATTGCACGGTATCCA | hsa-miR-363 |
| 75 | TCCGTTTTTTTTTTTACTCAGTA | 57 | CAGTCATTTGGGAAACCGTTACCATTAC | hsa-miR-451 |
| 76 | CGTTTTTTTTTTTACAGGCCG | 58 | CAGTCATTTGGCTATTGCACTTGTCCCG | hsa-miR-92a |
| 77 | CGTTTTTTTTTTTGGAGGCCG | 59 | CAGTCATTTGGGTATTGCACTCGTCCCG | hsa-miR-92b |
| 78 | CCGTTTTTTTTTTTCAACATCA | 60 | CAGTCATTTGGCTAGCTTATCAGACTGA | hsa-miR-21 |
| 79 | CCGTTTTTTTTTTTACAGTTCT | 61 | CAGTCATTTGGCAAGCTGCCAGTTGAAG | hsa-miR-22 |

TABLE 5-continued

Sequences of primers and probes used for the detection of differential miRs

| MGB SEQ ID NO: | MGB Sequence | FWD SEQ ID NO: | FWD | miR name |
|---|---|---|---|---|
| 80 | CCGTTTTTTTTTTTCAGACCGA | 62 | CAGTCATTTGGCCATTGCACTTGTCTCG | hsa-miR-25 |
| 81 | CCGTTTTTTTTTTTAGAGGCAG | 63 | CAGTCATTTGGCTGTCTGCCCGCATGCC | hsa-miR-346 |
| 82 | CCGTTTTTTTTTTTAAAGTCTC | 64 | CAGTCATTTGGCTGAGGGGCAGAGAGCG | hsa-miR-423-5p |
| 83 | AAAACCGATAGTGAGTCG | 65 | CGGGGCAGCTCAGTACAGGAT | hsa-miR-486-3p |
| 84 | AAAACCGATAGTGAGTCG | 66 | CCTCCCACACCCAAGGCTTGCA | hsa-miR-532-3p |
| 90 | CCGTTTTTTTTTTTAGCCTATC | 86 | CAGTCATTTGGCTTCAAGTAATCCAGGA | hsa-miR-26a |
| 91 | CGTTTTTTTTTTTGCAGAACT | 87 | CAGTCATTTGGGTTCACAGTGGCTAAGT | hsa-miR-27b |
| 92 | CCGTTTTTTTTTTTGAACAGAT | 88 | CAGTCATTTGGCCCCAGTGTTTAGACTA | hsa-miR-199b-5p |
| 93 | CCGTTTTTTTTTTTGCAATGCA | 89 | CAGTCATTTGGCGTGCATTGTAGTTGCA | hsa-miR-33a |
| 172 | CCGTTTTTTTTTTTAACCACAC | 147 | CAGTCATTTGGCTGAGGTAGTAGGTTGT | hsa-let-7b |
| 173 | CCGTTTTTTTTTTTAACTATAC | 148 | CAGTCATTTGGGTGAGGTAGTAGATTGT | hsa-let-7f |
| 174 | CCGTTTTTTTTTTTCACAGGTT | 149 | CAGTCATTTGGCTCCCTGAGACCCTTTA | hsa-miR-125a-5p |
| 175 | CCGTTTTTTTTTTTCGCATTAT | 150 | CAGTCATTTGGGTCGTACCGTGAGTAAT | hsa-miR-126 |
| 176 | CCGTTTTTTTTTTTCCGTGGTT | 151 | CAGTCATTTGGCTACCACAGGGTAGAAC | hsa-miR-140-3p |
| 177 | CCGTTTTTTTTTTTCCATAAAG | 152 | CAGTCATTTGGGTGTAGTGTTTCCTACT | hsa-miR-142-3p |
| 178 | CCGTTTTTTTTTTTACTAGACT | 153 | CAGTCATTTGGGTCGAGGAGCTCACAGT | hsa-miR-151-5p |
| 179 | CGTTTTTTTTTTTCAGCTGCT | 154 | CAGTCATTTGGGCAACGGAATCCCAAAA | hsa-miR-191 |
| 180 | CCGTTTTTTTTTTTGGGGTATT | 155 | CAGTCATTTGGCTGTCAGTTTGTCAAAT | hsa-miR-223 |
| 181 | CCGTTTTTTTTTTTGGAAATCC | 156 | CAGTCATTTGGCATCACATTGCCAGGGA | hsa-miR-23a |
| 182 | CCGTTTTTTTTTTTCTGTTCCT | 157 | CAGTCATTTGGCTGGCTCAGTTCAGCAG | hsa-miR-24 |
| 183 | CCGTTTTTTTTTTTGCGGAACT | 158 | CAGTCATTTGGCTTCACAGTGGCTAAGT | hsa-miR-27a |
| 184 | CCGTTTTTTTTTTTCTCAATAG | 159 | CAGTCATTTGGCAAGGAGCTCACAGTCT | hsa-miR-28-5p |
| 185 | CCGTTTTTTTTTTTAACCGATT | 160 | CAGTCATTTGGCTAGCACCATTTGAAAT | hsa-miR-29c |
| 186 | CCGTTTTTTTTTTTCTTCCAGT | 161 | CAGTCATTTGGGTGTAAACATCCCCGAC | hsa-miR-30d |

TABLE 5-continued

Sequences of primers and probes used for the detection of differential miRs

| MGB SEQ ID NO: | MGB Sequence | FWD SEQ ID NO: | FWD | miR name |
|---|---|---|---|---|
| 187 | CCGTTTTTTTTTTTGCTGTAAA | 162 | CAGTCATTTGGCCTTTCAGTCGGATGTT | hsa-miR-30e* |
| 188 | CCGTTTTTTTTTTTACTGGAGG | 163 | CAGTCATTTGGCCCTCTGGGCCCTTCCT | hsa-miR-326 |
| 189 | CCGTTTTTTTTTTTCTAGGATA | 164 | CAGTCATTTGGCGCCCCTGGGCCTATCC | hsa-miR-331-3p |
| 190 | CCGTTTTTTTTTTTACATTTTT | 165 | CAGTCATTTGGCTCAAGAGCAATAACGA | hsa-miR-335 |
| 191 | CCGTTTTTTTTTTTGTGGGTGT | 166 | CAGTCATTTGGCCACGCTCATGCACACA | hsa-miR-574-3p |
| 192 | CCGTTTTTTTTTTTGCTGTTAG | 167 | CAGTCATTTGGCTGCGGGGCTAGGGCTA | hsa-miR-744 |
| 193 | CCGTTTTTTTTTTTCGCAAGGT | 168 | CAGTCATTTGGCCACCCGTAGAACCGAC | hsa-miR-99b |
| 194 | CCGTTTTTTTTTTTGTCAGCAG | 169 | CAGTCATTTGGCTCACAATGCTGACACT | MID-00108 |
| 195 | CCGTTTTTTTTTTTCACATTCC | 170 | CAGTCATTTGGCTCTCCGGGGAGGCAGG | MID-00630 |
| 196 | AAAACCGATAGTGAGTCG | 171 | GCCTCCCACTGCTTCACTTGACTA | MID-24705 |
| | | 85 | Reverse complement | |

Recent studies suggest that microRNAs in the circulation are protected from the RNAse-rich environment either by protein complexes or by encapsulation in vesicles such as exosomes. To explore whether the differences observed in miRNA levels exist in the exosomal fraction, the levels of miRNAs were measured in sera from 10 HF patients and 10 controls processed with the Exoquick kit which enriches the sample with exosomal miRNAs. The differences in microRNA levels between HF and controls in the exosomal fraction were similar to those seen in the un-fractioned serum. Specifically, the top four miRNAs with elevated levels in un-fractioned serum of HF patients were also elevated in the exosomal fraction of HF patients relative to controls. However there was no increase in the strength of the differences (data not shown).

The four miRNAs which had the most significant ($p<0.0005$) increased levels in sera of HF patients when compared to sera of controls were: hsa-miR-423-5p, hsa-miR-22, hsa-miR-320a, and hsa-miR-92b. Box plots for these miRs are shown in FIGS. 1A-1D.

A score (miR-score) was calculated for each sample as the mean normalized-inverted signal of these 4 miRs and adjusted by subtracting a constant (the minimal score) so that the range of scores starts at 0. The miR-score was compared between HF and Control groups. The miR score allowed a significant separation between the HF and the control groups with a median score of 2.9 in the HF group and 1.3 in the Control group (FIG. 3). The ability of the miR-score to discriminate the HF group from Control group is characterized by the Receiver Operating Characteristic (ROC) curve with an Area under the ROC Curve (AUC) of 0.90 (FIG. 4). By classifying any score above 1.98 as "probable" HF patient we achieve sensitivity of 90% and specificity of 90% for identification of HF patient. Leave-one-out cross-validation with a logistic regression classifier using the miRNA-score to discriminate HF from controls yielded similar results (90% specificity and 87% sensitivity).

Example 3

MiRs' Score and Clinical Association

The miRs' score was tested for possible association with several clinical and prognostic parameters: age, gender, body mass index (BMI), ischemic etiology, Left ventricular ejection fraction (LVEF), New York Heart Association (NYHA) Functional Classification (NYHA), Left ventricular end diastolic dimension (EDD), Left atrial dimension (LAD), BNP serum levels and wide QRS width (≥120 ms) on the electrocardiogram. Analysis was performed as described in Example 1.

There was no significant association between the miRs' score and age ($p=0.58$), gender ($p=0.9$), BMI ($p=0.25$), ischemic etiology ($p=0.93$), LVEF ($p=0.37$) or NYHA ($p=0.35$). However, high miRs' score had a significant association with elevated serum BNP levels ($p=0.002$), wide QRS ($p=0.009$), EDD ($p=0.03$) and LAD ($p=0.01$), (FIGS. 6, 7, 8, 9 respectively). For serum BNP level, a strong correlation to the miR-score was observed ($r=0.63$; $p=0.0003$) (FIG. 5).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method of determining increased risk of chronic heart failure in a subject, the method comprising: providing a biological sample from a human subject; determining an expression profile in said sample by amplifying nucleic acid sequences comprising SEQ ID NOS: 4 and 13, wherein said amplification comprises contacting said biological sample with a forward primer comprising a nucleic acid of SEQ ID NO: 64; comparing said expression profile to a reference expression profile comprising expression levels of SEQ ID NOS: 4 and 13 in at least one biological sample from at least one control subject; detecting an increase in the level of SEQ ID NOS: 4 and 13 in said biological sample compared to said reference expression profile; and determining increased risk of chronic heart failure in the human subject based on detecting an increase in the level of SEQ ID NOs: 4 and 13.

2. The method of claim 1, further comprising detecting an increase in the level of a nucleic acid comprising SEQ ID NO: 3 in said biological sample compared to said reference expression profile, and determining an increased risk of chronic heart failure in the human subject based on detecting an increase in the level of SEQ ID NO: 3, wherein said reference expression profile comprises an expression level of SEQ ID NO: 3 in the at least one biological sample from the at least one control subject.

3. The method of claim 1, wherein said biological sample is a serum sample.

4. The method of claim 1, wherein the nucleic acid amplification method is real-time PCR, said PCR comprising forward and reverse primers.

5. The method of claim 4, wherein the real-time PCR method further comprises a probe.

6. The method of claim 5, wherein the probe comprises a nucleic acid sequence that is complementary to a sequence comprising any one of SEQ ID NOS: 4 and 13.

7. The method of claim 5, wherein the probe comprises a nucleic acid sequence comprising any one of SEQ ID NOS: 73 and 82.

8. The method of claim 4, wherein the reverse primer comprises a nucleic acid sequence comprising SEQ ID NO: 8.

9. The method of claim 1, further comprising managing subject treatment based on the heart disease status.

10. The method of claim 9, wherein managing subject treatment is selected from ordering further diagnostic tests, administering at least one therapeutic agent, surgery, and taking no further action.

11. The method of claim 1, said method comprising further detecting a decrease in the level of a nucleic acid comprising any one of SEQ ID NOS: 40, 100 and 108 in said biological sample compared to said reference expression profile, wherein said reference expression profile comprises an expression level of the any one of SEQ ID NOs: 40, 100 and 108 in the at least one biological sample from the at least one control subject.

12. The method of claim 11, further comprising determining increased risk of chronic heart failure based on detecting a decrease in the level of the at least one nucleic acid comprising any one of SEQ ID NOS: 40, 100, and 108 in said biological sample compared to said reference expression profile.

* * * * *